(12) United States Patent
Hansen et al.

(10) Patent No.: US 11,331,120 B2
(45) Date of Patent: May 17, 2022

(54) CANNULA ASSEMBLY KIT

(71) Applicant: 3DIntegrated Aps, København N. (DK)

(72) Inventors: Steen Møller Hansen, Skødstrup (DK); Henriette Schultz Kirkegaard, Copenhagen V (DK)

(73) Assignee: 3DIntegrated Aps, København N (DK)

( * ) Notice: Subject to any disclaimer, the term of this patent is extended or adjusted under 35 U.S.C. 154(b) by 691 days.

(21) Appl. No.: 15/589,476

(22) Filed: May 8, 2017

(65) Prior Publication Data

US 2017/0238962 A1     Aug. 24, 2017

Related U.S. Application Data

(63) Continuation of application No. PCT/DK2016/050234, filed on Jul. 1, 2016.

(51) Int. Cl.
*A61B 1/04* (2006.01)
*A61B 1/06* (2006.01)
(Continued)

(52) U.S. Cl.
CPC ............ *A61B 17/3421* (2013.01); *A61B 1/04* (2013.01); *A61B 1/05* (2013.01); *A61B 1/06* (2013.01);
(Continued)

(58) Field of Classification Search
CPC ....... A61B 17/3421; A61B 1/05; A61B 90/37; A61B 1/04; A61B 1/06; A61B 1/313;
(Continued)

(56) References Cited

U.S. PATENT DOCUMENTS

| 3,919,541 A | 11/1975 | Chao |
| 4,694,434 A | 9/1987 | Von Ramm et al. |
| (Continued) | | |

FOREIGN PATENT DOCUMENTS

| CA | 2 603 353 A1 | 9/2007 |
| CN | 2533818 Y | 2/2003 |
| (Continued) | | |

OTHER PUBLICATIONS

European Patent Application No. 16781653.7, by 3DIntegrated ApS: Supplementary European Search Report, dated May 22, 2017 (4 pages).

(Continued)

*Primary Examiner* — Timothy J Neal
*Assistant Examiner* — Genja M Frankert
(74) *Attorney, Agent, or Firm* — Mintz Levin Cohn Ferris Glovsky and Popeo, P.C.

(57) ABSTRACT

The invention comprises a cannula assembly kit for a trocar suitable for use in minimally invasive surgery. The cannula assembly kit comprises a cannula and a pattern generating member. The cannula has a distal end and a proximal end and comprises a flange portion at its proximal end and an elongate cannula shaft portion extending from said flange portion to its distal end and an access port through the flange portion and the elongate cannula shaft portion, such that a surgical tool of a surgical instrument can be inserted through the access port. The pattern generating member comprises a pattern light source and a projector arranged such that the pattern light source is operatively connected to the projector for projecting a light pattern. At least the projector of the pattern generating member is configured for being at least temporarily fixed to the cannula shaft portion of the cannula.

16 Claims, 17 Drawing Sheets

(51) Int. Cl.
*A61B 17/34* (2006.01)
*A61B 90/30* (2016.01)
*A61B 1/313* (2006.01)
*A61B 1/05* (2006.01)
*A61B 90/00* (2016.01)
*A61B 34/30* (2016.01)
*A61B 34/20* (2016.01)

(52) U.S. Cl.
CPC .............. *A61B 1/313* (2013.01); *A61B 90/30* (2016.02); *A61B 90/37* (2016.02); *A61B 2017/3445* (2013.01); *A61B 2017/3447* (2013.01); *A61B 2017/3449* (2013.01); *A61B 2034/2065* (2016.02); *A61B 2034/302* (2016.02); *A61B 2090/306* (2016.02); *A61B 2090/309* (2016.02); *A61B 2090/373* (2016.02)

(58) Field of Classification Search
CPC ............ A61B 90/30; A61B 2017/3447; A61B 2017/3449; A61B 2034/302; A61B 2017/3445; A61B 2034/2065; A61B 2090/306; A61B 2090/373; A61B 2090/309
See application file for complete search history.

(56) References Cited

U.S. PATENT DOCUMENTS

| | | |
|---|---|---|
| 4,877,016 A | 10/1989 | Kantor et al. |
| 4,887,222 A | 12/1989 | Miyake et al. |
| 5,457,439 A | 10/1995 | Kuhn |
| 5,588,949 A * | 12/1996 | Taylor ................ A61B 1/00193 600/101 |
| 5,651,783 A | 7/1997 | Reynard |
| 5,710,870 A | 1/1998 | Ohm et al. |
| 5,725,523 A | 3/1998 | Mueller |
| 5,747,953 A | 5/1998 | Philipp |
| 5,754,717 A | 5/1998 | Esch |
| 5,769,791 A * | 6/1998 | Benaron ............... A61B 5/0084 600/473 |
| 5,836,869 A | 11/1998 | Kudo et al. |
| 5,888,194 A | 3/1999 | Utsumi et al. |
| 5,933,223 A | 8/1999 | Flock et al. |
| 5,951,142 A | 9/1999 | Wang et al. |
| 5,976,077 A | 11/1999 | Wittens et al. |
| 5,989,181 A | 11/1999 | Duetting et al. |
| 6,006,127 A | 12/1999 | Van Der Brug et al. |
| 6,017,354 A | 1/2000 | Culp et al. |
| 6,036,636 A | 3/2000 | Motoki et al. |
| 6,165,184 A * | 12/2000 | Verdura .................. A61B 17/34 606/148 |
| 6,361,530 B1 | 3/2002 | Mersch |
| 6,387,044 B1 * | 5/2002 | Tachibana .......... A61B 1/00135 600/114 |
| 6,471,638 B1 | 10/2002 | Chang et al. |
| 6,494,827 B1 | 12/2002 | Matsumoto et al. |
| 6,522,806 B1 | 2/2003 | James, IV et al. |
| 6,527,704 B1 | 3/2003 | Chang et al. |
| 6,537,290 B2 | 3/2003 | Adams et al. |
| 6,549,288 B1 | 4/2003 | Migdal et al. |
| 6,631,271 B1 | 10/2003 | Logan |
| 6,659,943 B2 | 12/2003 | Watanabe et al. |
| 6,741,883 B2 | 5/2004 | Gildenberg |
| 6,791,601 B1 | 9/2004 | Chang et al. |
| 6,810,184 B2 | 10/2004 | Skutnik |
| 6,811,546 B1 | 11/2004 | Callas et al. |
| 6,908,428 B2 | 6/2005 | Aizenfeld et al. |
| 6,945,981 B2 | 9/2005 | Donofrio et al. |
| 7,037,314 B2 | 5/2006 | Armstrong |
| 7,049,594 B2 | 5/2006 | Wu et al. |
| 7,063,695 B2 | 6/2006 | Nield et al. |
| 7,113,675 B2 | 9/2006 | Nield et al. |
| 7,211,044 B2 | 5/2007 | Mast et al. |
| 7,422,327 B2 * | 9/2008 | Smith ...................... A61B 3/12 351/205 |
| 7,464,846 B2 | 12/2008 | Shelton, IV et al. |
| 7,505,808 B2 | 3/2009 | Anderson et al. |
| 7,725,214 B2 | 5/2010 | Diolaiti |
| 7,775,969 B2 | 8/2010 | Teichmann |
| 7,784,947 B2 | 8/2010 | Perez et al. |
| 7,843,558 B2 | 11/2010 | Furman |
| 7,845,537 B2 | 12/2010 | Shelton, IV et al. |
| 7,876,942 B2 | 1/2011 | Gilboa |
| 7,912,532 B2 | 3/2011 | Schmidt et al. |
| 7,927,272 B2 | 4/2011 | Bayer et al. |
| 7,976,459 B2 | 7/2011 | Laser |
| 8,064,819 B2 | 11/2011 | Ingrassia et al. |
| 8,086,008 B2 | 12/2011 | Coste-maniere et al. |
| 8,162,826 B2 | 4/2012 | Pecherer et al. |
| 8,165,351 B2 | 4/2012 | Bendall |
| 8,182,422 B2 | 5/2012 | Bayer et al. |
| 8,211,044 B2 | 7/2012 | Liebowitz |
| 8,242,390 B2 | 8/2012 | Prest et al. |
| 8,242,398 B2 | 8/2012 | Young et al. |
| 8,340,379 B2 | 12/2012 | Razzaque et al. |
| 8,397,335 B2 | 3/2013 | Gordin et al. |
| 8,403,843 B2 | 3/2013 | Bruto Da Costa |
| 8,409,076 B2 | 4/2013 | Pang et al. |
| 8,443,007 B1 | 5/2013 | Kindig et al. |
| 8,480,566 B2 | 7/2013 | Farr |
| 8,512,368 B2 | 8/2013 | Sato et al. |
| 8,525,059 B2 | 9/2013 | Berger et al. |
| 8,527,033 B1 | 9/2013 | Williams et al. |
| 8,531,511 B2 | 9/2013 | Katakura |
| 8,554,307 B2 | 10/2013 | Razzaque et al. |
| 8,568,304 B2 | 10/2013 | Vayser et al. |
| 8,632,535 B2 | 1/2014 | Shelton, IV et al. |
| 8,657,809 B2 | 2/2014 | Schoepp |
| 8,670,816 B2 | 3/2014 | Green et al. |
| 8,672,207 B2 | 3/2014 | Shelton, IV et al. |
| 8,708,211 B2 | 4/2014 | Zemlok et al. |
| 8,721,525 B2 | 5/2014 | Heckele et al. |
| 8,750,568 B2 | 6/2014 | Frank et al. |
| 8,780,362 B2 | 7/2014 | Sharonov et al. |
| 8,880,151 B1 | 11/2014 | Stolka et al. |
| 8,892,191 B2 | 11/2014 | Brennan et al. |
| 8,922,781 B2 | 12/2014 | Tearney et al. |
| 8,968,347 B2 | 3/2015 | McCollam |
| 8,988,505 B2 | 3/2015 | Schaerer et al. |
| 9,008,757 B2 | 4/2015 | Wu |
| 9,179,984 B2 | 11/2015 | Teichman et al. |
| 2001/0025174 A1 | 9/2001 | Daniel et al. |
| 2001/0027272 A1 | 10/2001 | Saito et al. |
| 2001/0040990 A1 | 11/2001 | Dadi |
| 2001/0055462 A1 | 12/2001 | Seibel |
| 2002/0028986 A1 | 3/2002 | Thompson |
| 2002/0049435 A1 | 4/2002 | Mersch |
| 2002/0049464 A1 | 4/2002 | Donofrio et al. |
| 2002/0087179 A1 | 7/2002 | Culp et al. |
| 2002/0123665 A1 | 9/2002 | Miller |
| 2002/0137987 A1 | 9/2002 | Watanabe et al. |
| 2003/0013960 A1 | 1/2003 | Makin et al. |
| 2003/0029464 A1 | 2/2003 | Chen et al. |
| 2003/0095781 A1 | 5/2003 | Williams |
| 2003/0118302 A1 | 6/2003 | James, IV et al. |
| 2004/0022527 A1 | 2/2004 | Carusillo et al. |
| 2004/0064019 A1 | 4/2004 | Chang et al. |
| 2004/0122292 A1 | 6/2004 | Dey et al. |
| 2004/0145746 A1 | 7/2004 | Kim et al. |
| 2004/0188616 A1 | 9/2004 | Wu et al. |
| 2005/0004592 A1 * | 1/2005 | Criscuolo .......... A61B 17/0218 606/190 |
| 2005/0005024 A1 | 1/2005 | Samuels et al. |
| 2005/0054894 A1 | 3/2005 | Aizenfeld et al. |
| 2005/0085718 A1 | 4/2005 | Shahidi |
| 2005/0131426 A1 | 6/2005 | Moctezuma de la Barrera et al. |
| 2005/0135749 A1 | 6/2005 | Nield et al. |
| 2006/0004406 A1 | 1/2006 | Wehrstein et al. |
| 2006/0036162 A1 | 2/2006 | Shahidi et al. |
| 2006/0069314 A1 | 3/2006 | Farr |
| 2006/0114473 A1 | 6/2006 | Tearney et al. |
| 2006/0171693 A1 | 8/2006 | Todd et al. |

(56) References Cited

U.S. PATENT DOCUMENTS

| | | |
|---|---|---|
| 2006/0235270 A1 | 10/2006 | Teichmann |
| 2006/0235279 A1* | 10/2006 | Hawkes .................. A61B 1/32 600/222 |
| 2006/0241347 A1 | 10/2006 | Whitehead |
| 2006/0258938 A1 | 11/2006 | Hoffman et al. |
| 2007/0060098 A1 | 3/2007 | Mccoy |
| 2007/0112336 A1 | 5/2007 | Aizenfeld et al. |
| 2007/0112337 A1 | 5/2007 | Salman et al. |
| 2007/0147707 A1 | 6/2007 | Coste-Maniere et al. |
| 2007/0151390 A1 | 7/2007 | Blumenkranz et al. |
| 2007/0167679 A1 | 7/2007 | Miyamoto et al. |
| 2007/0175964 A1 | 8/2007 | Shelton, IV et al. |
| 2007/0179488 A1 | 8/2007 | Trusty et al. |
| 2007/0206275 A1 | 9/2007 | Hemmer et al. |
| 2007/0225550 A1 | 9/2007 | Gattani et al. |
| 2007/0250006 A1 | 10/2007 | Court et al. |
| 2007/0255101 A1 | 11/2007 | Bar-or |
| 2007/0260121 A1 | 11/2007 | Bakos et al. |
| 2008/0009677 A1 | 1/2008 | Shoroji et al. |
| 2008/0058989 A1 | 3/2008 | Oleynikov et al. |
| 2008/0071140 A1 | 3/2008 | Gattani et al. |
| 2008/0159653 A1 | 7/2008 | Dunki-jacobs et al. |
| 2008/0167522 A1 | 7/2008 | Giordano et al. |
| 2008/0167671 A1 | 7/2008 | Giordano et al. |
| 2008/0188716 A1 | 8/2008 | Heckele et al. |
| 2008/0208006 A1 | 8/2008 | Farr |
| 2008/0208041 A1 | 8/2008 | Gilboa |
| 2008/0319311 A1 | 12/2008 | Hamadeh |
| 2009/0017430 A1 | 1/2009 | Muller-daniels et al. |
| 2009/0036744 A1* | 2/2009 | Vayser .................. A61B 1/32 600/182 |
| 2009/0054767 A1 | 2/2009 | Telischak et al. |
| 2009/0192519 A1 | 7/2009 | Omori |
| 2009/0203991 A1 | 8/2009 | Papaioannou et al. |
| 2009/0209998 A1 | 8/2009 | Widmann |
| 2009/0218527 A1 | 9/2009 | French et al. |
| 2009/0225320 A1 | 9/2009 | Bendall et al. |
| 2009/0240111 A1 | 9/2009 | Kessler et al. |
| 2009/0244260 A1 | 10/2009 | Takahashi et al. |
| 2009/0248041 A1 | 10/2009 | Williams et al. |
| 2009/0270682 A1 | 10/2009 | Visser |
| 2009/0318756 A1 | 12/2009 | Fisher et al. |
| 2009/0318758 A1* | 12/2009 | Farr .................. A61B 1/0638 600/112 |
| 2009/0318763 A1 | 12/2009 | Koerner et al. |
| 2009/0323053 A1 | 12/2009 | Furman |
| 2010/0036393 A1 | 2/2010 | Unsworth |
| 2010/0065605 A1 | 3/2010 | Shelton, VI et al. |
| 2010/0065609 A1 | 3/2010 | Schwemberger |
| 2010/0069920 A1 | 3/2010 | Naylor et al. |
| 2010/0096435 A1 | 4/2010 | Fuchs et al. |
| 2010/0106015 A1 | 4/2010 | Norris |
| 2010/0200636 A1 | 8/2010 | Zemlok et al. |
| 2010/0228092 A1 | 9/2010 | Ortiz et al. |
| 2010/0268067 A1 | 10/2010 | Razzaque et al. |
| 2011/0069159 A1 | 3/2011 | Soler et al. |
| 2011/0110114 A1 | 5/2011 | Papac et al. |
| 2011/0112377 A1* | 5/2011 | Papac .................. A61B 3/12 600/249 |
| 2011/0161054 A1 | 6/2011 | Woolf et al. |
| 2011/0165535 A1 | 7/2011 | Berger et al. |
| 2011/0208004 A1 | 8/2011 | Feingold et al. |
| 2011/0237915 A1 | 9/2011 | Yamaguchi |
| 2011/0275901 A1 | 11/2011 | Shelton, IV |
| 2011/0282160 A1 | 11/2011 | Bhadri et al. |
| 2011/0319714 A1 | 12/2011 | Roelle et al. |
| 2012/0024934 A1 | 2/2012 | Shelton, IV et al. |
| 2012/0062724 A1 | 3/2012 | Yokota |
| 2012/0071711 A1 | 3/2012 | Shelton et al. |
| 2012/0071757 A1 | 3/2012 | Salcudean et al. |
| 2012/0082970 A1 | 4/2012 | Pravong et al. |
| 2012/0101497 A1 | 4/2012 | Jayaraj |
| 2012/0108901 A1 | 5/2012 | Sargeant et al. |
| 2012/0116369 A1 | 5/2012 | Viola |
| 2012/0130162 A1 | 5/2012 | Dolt et al. |
| 2012/0143049 A1 | 6/2012 | Neubauer et al. |
| 2012/0184951 A1 | 7/2012 | Viola |
| 2012/0209123 A1 | 8/2012 | King |
| 2012/0238808 A1 | 9/2012 | Teichtmann |
| 2012/0265009 A1 | 10/2012 | Yang et al. |
| 2012/0265010 A1 | 10/2012 | Uram |
| 2012/0265022 A1* | 10/2012 | Menn .................. A61B 17/3421 600/246 |
| 2012/0265071 A1 | 10/2012 | Berke |
| 2012/0296163 A1 | 11/2012 | Stopek |
| 2012/0302828 A1 | 11/2012 | Toledo-crow et al. |
| 2013/0038836 A1* | 2/2013 | Smith .................. A61B 3/0008 351/211 |
| 2013/0053782 A1* | 2/2013 | Shelton, IV ....... A61B 17/3421 604/167.03 |
| 2013/0053835 A1 | 2/2013 | Bacher et al. |
| 2013/0060084 A1 | 3/2013 | Fouts et al. |
| 2013/0070070 A1 | 3/2013 | Katakura |
| 2013/0103023 A1 | 4/2013 | Monson et al. |
| 2013/0110005 A1* | 5/2013 | Sharonov ............. A61B 5/0084 600/587 |
| 2013/0110006 A1 | 5/2013 | Sharonov et al. |
| 2013/0110129 A1 | 5/2013 | Reid et al. |
| 2013/0123800 A1 | 5/2013 | Leroy et al. |
| 2013/0123801 A1 | 5/2013 | Umasuthan et al. |
| 2013/0144267 A1 | 6/2013 | Chan et al. |
| 2013/0190759 A1 | 7/2013 | Waaler et al. |
| 2013/0197317 A1 | 8/2013 | Daniel et al. |
| 2013/0218024 A1 | 8/2013 | Boctor et al. |
| 2013/0226037 A1 | 8/2013 | Pinto et al. |
| 2013/0226156 A1 | 8/2013 | Sharonov |
| 2013/0267787 A1 | 10/2013 | Warnock |
| 2013/0267975 A1 | 10/2013 | Timm et al. |
| 2013/0281845 A1 | 10/2013 | Luiken |
| 2013/0296712 A1 | 11/2013 | Durvasula |
| 2013/0317351 A1 | 11/2013 | Case et al. |
| 2013/0317352 A1 | 11/2013 | Case et al. |
| 2013/0317353 A1 | 11/2013 | Frank et al. |
| 2013/0324999 A1 | 12/2013 | Price et al. |
| 2013/0345513 A1 | 12/2013 | Tsuruta et al. |
| 2014/0005484 A1 | 1/2014 | Charles |
| 2014/0005682 A1 | 1/2014 | Worrell et al. |
| 2014/0012078 A1 | 1/2014 | Coussa |
| 2014/0012286 A1 | 1/2014 | Lee et al. |
| 2014/0025067 A1 | 1/2014 | Kerr et al. |
| 2014/0030669 A1 | 1/2014 | Hey et al. |
| 2014/0031665 A1 | 1/2014 | Pinto et al. |
| 2014/0051994 A1 | 2/2014 | Graumann et al. |
| 2014/0052005 A1 | 2/2014 | Yokota |
| 2014/0066784 A1 | 3/2014 | Yokota |
| 2014/0071239 A1 | 3/2014 | Yokota |
| 2014/0071257 A1 | 3/2014 | Yokota |
| 2014/0074116 A1 | 3/2014 | Collins |
| 2014/0088410 A1 | 3/2014 | Wu |
| 2014/0106626 A1 | 4/2014 | Frushour et al. |
| 2014/0107417 A1 | 4/2014 | McKinley et al. |
| 2014/0107471 A1 | 4/2014 | Haider et al. |
| 2014/0107685 A1 | 4/2014 | O'neill et al. |
| 2014/0114327 A1 | 4/2014 | Boudreaux et al. |
| 2014/0121507 A1 | 5/2014 | Nau, Jr. |
| 2014/0121508 A1 | 5/2014 | Latimer et al. |
| 2014/0148799 A1 | 5/2014 | Mueller |
| 2014/0163359 A1 | 6/2014 | Sholev et al. |
| 2014/0171962 A1 | 6/2014 | Kang |
| 2014/0180001 A1 | 6/2014 | Von Grunberg et al. |
| 2014/0194896 A1 | 7/2014 | Frimer et al. |
| 2014/0200406 A1 | 7/2014 | Bennett et al. |
| 2014/0200561 A1 | 7/2014 | Ingmanson et al. |
| 2014/0204702 A1 | 7/2014 | Ratering |
| 2014/0207002 A1 | 7/2014 | Seow |
| 2014/0235946 A1 | 8/2014 | Smith |
| 2014/0236177 A1 | 8/2014 | Verner et al. |
| 2014/0243658 A1 | 8/2014 | Breisacher et al. |
| 2014/0275764 A1 | 9/2014 | Shen et al. |
| 2014/0275771 A1 | 9/2014 | Henley et al. |
| 2014/0276097 A1 | 9/2014 | Sharonov |
| 2014/0276532 A1* | 9/2014 | Zook .................. A61B 17/3403 604/500 |
| 2014/0296636 A1 | 10/2014 | Hatano |

(56) References Cited

U.S. PATENT DOCUMENTS

| | | |
|---|---|---|
| 2014/0303491 A1 | 10/2014 | Shekhar et al. |
| 2014/0316206 A1* | 10/2014 | Vasan .................. A61B 1/0669 600/191 |
| 2014/0357945 A1 | 12/2014 | Duckworth |
| 2014/0367444 A1 | 12/2014 | Williams |
| 2014/0367591 A1 | 12/2014 | Mahou et al. |
| 2015/0005748 A1 | 1/2015 | Sniffin et al. |
| 2015/0018622 A1 | 1/2015 | Tesar et al. |
| 2015/0049907 A1 | 2/2015 | Hong et al. |
| 2015/0065875 A1 | 3/2015 | Friebe |
| 2015/0069108 A1 | 3/2015 | Williams |
| 2015/0073398 A1 | 3/2015 | Toledo-Crow et al. |
| 2015/0076211 A1 | 3/2015 | Irka et al. |
| 2015/0080660 A1 | 3/2015 | Gomez et al. |
| 2015/0080764 A1 | 3/2015 | Poe |
| 2015/0086162 A1 | 3/2015 | Miyahara et al. |
| 2015/0088115 A1 | 3/2015 | Smith |
| 2015/0109427 A1 | 4/2015 | Wood et al. |
| 2015/0119637 A1 | 4/2015 | Alvarez et al. |
| 2015/0133960 A1 | 5/2015 | Lohmeier et al. |
| 2015/0173591 A1 | 6/2015 | Zheng et al. |
| 2015/0230866 A1 | 8/2015 | Tung et al. |
| 2015/0238276 A1 | 8/2015 | Atarot et al. |
| 2015/0265792 A1 | 9/2015 | Goudra et al. |
| 2015/0359418 A1 | 12/2015 | Feussner et al. |
| 2016/0081712 A1 | 3/2016 | Heniford et al. |
| 2016/0166345 A1 | 6/2016 | Kumar et al. |
| 2016/0270757 A1 | 9/2016 | Toma et al. |
| 2016/0278611 A1 | 9/2016 | Power |
| 2016/0360954 A1* | 12/2016 | Rohling .................. A61B 34/20 |
| 2017/0055819 A1 | 3/2017 | Hansen et al. |
| 2017/0095269 A1 | 4/2017 | Reid et al. |
| 2017/0105802 A1 | 4/2017 | Taraschi et al. |
| 2017/0172382 A1 | 6/2017 | Nir et al. |
| 2017/0251900 A1 | 9/2017 | Hansen et al. |
| 2018/0014851 A1 | 1/2018 | Hansen et al. |
| 2018/0042686 A1 | 2/2018 | Peine |
| 2018/0075612 A1* | 3/2018 | Michielin .......... G02B 23/2461 |
| 2018/0325604 A1 | 11/2018 | Atarot et al. |

FOREIGN PATENT DOCUMENTS

| | | |
|---|---|---|
| CN | 2691487 Y | 4/2005 |
| CN | 1729938 A | 2/2006 |
| CN | 101305901 A | 11/2008 |
| CN | 201316257 Y | 9/2009 |
| CN | 201393995 Y | 2/2010 |
| CN | 201393999 Y | 2/2010 |
| CN | 201602746 U | 10/2010 |
| CN | 101991399 A | 3/2011 |
| CN | 201861616 U | 6/2011 |
| CN | 102401646 A | 4/2012 |
| CN | 102626301 A | 8/2012 |
| CN | 103299355 A | 9/2013 |
| CN | 203379100 U | 1/2014 |
| CN | 203852327 U | 10/2014 |
| DE | 20002770 U1 | 10/2000 |
| DE | 102004008488 A1 | 9/2004 |
| DE | 102005045706 B3 | 4/2007 |
| DE | 102007007742 A1 | 8/2008 |
| DE | 102008056830 A1 | 5/2010 |
| DE | 202011103007 U1 | 11/2011 |
| DE | 102012209448 A1 | 12/2013 |
| DE | 102012209450 A1 | 12/2013 |
| EP | 2 412 290 A1 | 2/2012 |
| EP | 1961372 B1 | 3/2012 |
| EP | 2554103 A1 | 2/2013 |
| EP | 2 630 915 A1 | 8/2013 |
| EP | 2551698 B1 | 9/2014 |
| EP | 3056934 A1 | 8/2016 |
| FR | 2851701 A1 | 8/2004 |
| JP | 2000-131623 A | 5/2000 |
| JP | 2001-025469 A | 1/2001 |
| JP | 2003-061970 A | 3/2003 |
| JP | 2006-271600 A | 10/2006 |
| JP | 2015-073663 A | 4/2015 |
| WO | WO 95/10218 A1 | 4/1995 |
| WO | 00/42906 A2 | 7/2000 |
| WO | 01/52720 A1 | 7/2001 |
| WO | WO 02/080773 A1 | 10/2002 |
| WO | 2005/122940 A1 | 12/2005 |
| WO | WO 2009/116969 A1 | 9/2009 |
| WO | WO 2009/134634 A2 | 11/2009 |
| WO | 2012/072112 A1 | 6/2012 |
| WO | WO 2012/083247 A1 | 6/2012 |
| WO | 2013/002050 A1 | 1/2013 |
| WO | 2013/096896 A1 | 6/2013 |
| WO | WO 2013/163391 A1 | 10/2013 |
| WO | WO 2014/140813 A1 | 9/2014 |
| WO | 2014/174726 A1 | 10/2014 |
| WO | 2014/198675 A1 | 12/2014 |
| WO | 2015/124159 A1 | 8/2015 |
| WO | WO 2015/133958 A1 | 9/2015 |
| WO | WO 2015/135055 A1 | 9/2015 |
| WO | 2015/149041 A1 | 10/2015 |
| WO | 2016/019424 A1 | 2/2016 |
| WO | WO 2016/018815 A1 | 2/2016 |
| WO | WO 2016/057989 A2 | 4/2016 |

OTHER PUBLICATIONS

European Patent Application No. 17169285.8 by 3dintegrated ApS: Extended European Search Report and European Search Opinion, dated Aug. 31, 2017 (7 pages).

Albitar, C. et al. (2007) "Robust Structured Light Coding for 3D Reconstruction" *Proceedings of the 2007 IEEE 11th International Conference on Computer Vision (ICCV 2007)*, Oct. 14-21, 2007, Rio de Janeiro, Brazil; pp. 1-6, DOI: 10.1109/ICCV.2007.4408982.

Edgcumbe, P. et al. (2014) "Pico Lantern: A Pick-up Projector for Augmented Reality in Laparoscopic Surgery" Medical Image Computing and Computer-Assisted Intervention (MICCAI) 17th International Conference, Boston, MA, USA, Sep. 14-18, 2014, Proceedings. P. Golland et al. (Eds.): *MICCAI 2014, Part 1, LNCS* 8673, pp. 432-439.

Hao, W. (Dec. 2011) *Wide Baseline Stereo Image Rectification and Matching*. Dissertation. The University of Tennessee, Knoxville, Tennessee; 175 pages.

Kang, H. (May 2002) *Robotic Assisted Suturing in Minimally Invasive Surgery*. Thesis. Rensselaer Polytechnic Institute, Troy, New York; 183 pages.

Krupa, A. et al. (2002) "Autonomous retrieval and positioning of surgical instruments in robotized laparoscopic surgery using visual servoing and laser pointers" *Proceedings of the 2002 IEEE International Conference on Robotics and Automation*, May 11-15, 2002, Washington, DC; vol. 4, pp. 3769-3774.

Louw, M. and F. Nicolls (2005) "An approximate EM Homographical Iterative Closest Point algorithm" PRASA2005, Langebaan, Cape Town; p. 89-92 [online]. Available from: http://dip.ee.uct.ac.za/~nicolls/publish/ml05-prasa.pdf.

Pellicanò, N. et al. (2016) "Robust Wide Baseline Pose Estimation from Video (Supplementary Material)" *Proceedings of the International Conference on Pattern Recognition (ICPR)*, Dec. 4-8, 2016; 2 pages.

Pritchett, P. and A. Zisserman (1998) "Wide Baseline Stereo Matching" *Proceedings of the Sixth International Conference on Computer Vision*, Jan. 4-7, 1998; pp. 754-760.

Reiter, A. et al. (2014) "Surgical Structured Light for 3D Minimally Invasive Surgical Imaging" *Proceedings of the IEEE/RSJ International Conference on Intelligent Robots and Systems (IROS 2014)*; pp. 1282-1287.

Zhang, K. et al. (Sep. 2009) "A Surface Topology and Motion Compensation System for Microsurgery Guidance and Intervention based on Common-Path Optical Coherence Tomography" *IEEE Trans Biomed Eng*, 56(9):2318-2321. NIH Public Access Author Manuscript; available in PMC Sep. 1, 2010 (12 pages).

Supplementary European Search Report issued in European Patent Application No. 16853132.5, dated Oct. 27, 2017, 4 pages.

(56) References Cited

OTHER PUBLICATIONS

Ackerman et al., "Surface reconstruction of abdominal organs using laparoscopic structured light for augmented reality", Proceedings of SPIE, 2002, 4661:39-46.
Bauer et al., "Real-Time Range Imaging in Health Care: A Survey" Time-of-Flight and Depth Imaging. Sensors, Algorithms, and Applications. Dagstuhl Seminar 2012 and GCPR Workshop on Imaging New Modalities, Lecture Notes in Computer Science, 2013, 8200:188-212.
Choi et al., "An effective visualization technique for depth perception in augmented reality-based surgical navigation", International Journal of Medical Robotics and Computer Assisted Surgery, May 5, 2015, 12(1).
Clancy et al., "Spectrally encoded fiber-based structured lighting probe for intraoperative 3D imaging", Biomedical Optics Express, 2011, 2(11):3119-3128.
Geng et al., "Structured-light 3D surface imaging: a tutorial", Advances in Optics and Photonics, 2011, 3:128-160.
Karjee et al., "Spatial Data Estimation in Three-Dimensional Distributed Wireless Sensor Networks", International Conference on Embedded Systems, Jul. 3-4, 2014.
Maier-Hein et al., "Comparative Validation of Single-shot Optical Techniques for Laparoscopic 30 Surface Reconstruction", IEEE Transactions on Medical Imaging, Oct. 2014, 33(10):1913-1930.
Maier-Hein et al., "Optical techniques for 30 surface reconstructions in computer-assisted laparoscopic surgery", Medical Image Analysis, 2013, 17(8):974-996.
Maurice et al., "Real-time structured light coding for adaptive patterns", J. Real-Time Image Proc, 2013, 8:169-178.
Nicolau et al., "Augmented reality in laparoscopic surgical oncology", Surgical Oncology, Sep. 2011, 20(3):189-201.
"International Search Report and Written Opinion received for PCT/DK2016/050180", dated Apr. 11, 2016, 18 pages.
Salvi et al., "Pattern codification strategies in structure light systems", Pattern Recognition, Apr. 2004, 37(4):827-849.
Schmalz et al., "An endoscopic 30 scanner based on structured light", Medical Image Analysis, 2012, 16:1063-1072.
Extended European Search Report received for European Patent Application No. 17884041.9, dated Aug. 12, 2020, 11 pages.
Pennington et al. (Jul. 2001) "Miniaturized 3-D Surface Profilometer using a Fiber Optic Coupler", Optics & Laser Technology, 33(5):313-320.
Schick et al. (May 26, 2011) "3D Measuring in the Field of Endoscopy", Proceedings of SPIE, 8082:808216-1-80821: 6-12.
Su et al. (Aug. 26, 2015) "Three-dimensional Shape Measurements using Endoscopes", Proceedings of SPIE, 9586:95861H-1-95861H-6.
U.S. Appl. No. 15/120,256, filed Aug. 19, 2016, Set Comprising a Surgical Instrument.
U.S. Appl. No. 15/717,088, filed Sep. 27, 2017, Minimally Invasive Surgery System.
U.S. Appl. No. 15/601,276, filed May 22, 2017, Depiction System.

\* cited by examiner

CANNULA ASSEMBLY KIT

This application is a continuation of PCT International Application No. PCT/DK2016/050234, entitled, "CANNULA ASSEMBLY KIT, TROCAR ASSEMBLY KIT, SLEEVE ASSEMBLY, MINIMALLY INVASIVE SURGERY SYSTEM AND METHOD THEREFOR", with an international filing date of Jul. 1, 2016, claiming priority to PA 2015 70483 DK filed on Jul. 21, 2015.

TECHNICAL FIELD

The invention relates to a cannula assembly kit for a trocar suitable for use in minimally invasive surgery, a trocar assembly kit comprising such cannula assembly kit, a system comprising the cannula assembly kit and a sleeve assembly for such cannula assembly kit.

BACKGROUND ART

Minimally invasive surgery has been used increasingly in recent years due to the benefits compared to conventional open surgery as it reduces the trauma to the patient tissue, leaves smaller scars, minimizes post-surgical pain and enables a faster recovery of the patient.

For example, in laparoscopic surgery which is a typical form of minimally invasive surgery the surgeon accesses a body cavity, such as the abdominal or pelvic cavity, through a series of small incisions. A laparoscope is inserted through an incision, and conventionally connected to a monitor, thereby enabling the surgeon to see the inside of the abdominal or pelvic cavity. In order to perform the surgical procedure, surgical instruments are inserted through other incisions. In addition, the body cavity around the surgical site is inflated with a fluid, preferably gas e.g. carbon dioxide in order to create an 'air' space within the cavity to make space for the surgeon to view the surgical site and move the laparoscopic instruments.

Invasive surgeries are generally performed through rather small openings in a patient's skin and the surgical site is visualized for the surgeon by inserting a camera, such as an endoscope into the body cavity and displaying the images on a screen.

In order to improve the vision for surgeon, in particular to make it easier for the surgeon to determine the sizes of various organs, tissues, and other structures in a surgical site, several in-situ surgical metrology methods have been provided in the prior art. Different types of optical systems have been applied to provide an improved vision of the surgical site, which is approaching a 3D vision.

US2014276097 describes a system and method for performing optical measurements within a body cavity during minimal surgery. The system comprises a light source configured to emit a light beam, a first pattern generator defining a first longitudinal axis and configured to project a first generated pattern, and a second pattern generator defining a second longitudinal axis and configured to project a second generated pattern. The first and second generated patterns have different angular divergences. The first pattern generator is a diffractive circle pattern generator, whereas the second pattern generator is a diffractive cross pattern generator. Adjustment of the first and second generated patterns with respect to each other causes the system to serve as an optical ruler for performing the optical measurements when the first and second generate patterns overlap or coincide with each other at certain points.

EP 2630915 describes a light instrument for use in minimally invasive surgery, where the instrument includes an elongate tubular member and a metrology system mounted on the elongate tubular member. The metrology system includes a mask, a zoom lens assembly and a light element arranged such that the light element propagates light beams through the mask and the zoom lens assembly to project the patterns of the mask onto the surgical site of interest to provide markings as references used for measuring by the surgeon.

US 2013/0296712 describes an apparatus for determining endoscopic dimensional measurements, including a light source for projecting light patterns on a surgical sight including shapes with actual dimensional measurements and fiducials, and means for analyzing the projecting light patterns on the surgical site by comparing the actual dimensional measurements of the projected light patterns to the surgical site.

WO 2013/163391 describes at system for generating an image, which the surgeon can use for measuring the size of or distance between structures in the surgical field by using an invisible light for marking a pattern to the surgical field.

The system comprises a first camera; a second camera; a light source producing light at a frequency invisible to human eye; a dispersion unit projecting a predetermined pattern of light from the invisible light source; an instrument projecting the predetermined pattern of invisible light onto a target area; a band pass filter directing visible light to the first camera and the predetermined pattern of invisible light to the second camera; wherein the second camera images the target area and predetermined pattern of invisible light, and computes a three-dimensional image.

DISCLOSURE OF INVENTION

In an embodiment is provided a solution for providing good visibility of a body cavity during minimally invasive surgery in particular with respect to providing good visual information to the surgeon about the position of the surgical instrument relative to the surgical site.

In an embodiment is provided a tool for use in minimally invasive surgery, which tool can increase the visibility of a body cavity to thereby make it simpler for a surgeon to determine the position of a surgical instrument relative to the surgical site and thereby to increase the surgeon's control of movements of the surgical instrument relative to the surgical site.

In an embodiment is provided a tool for providing an increased visibility of the position of a surgical instrument relative to the surgical site, which tool is simple to use and can be produced at an adequate cost.

It has been found that the invention or embodiments thereof have a number of additional advantages, which will be clear to the skilled person from the following description.

It has been found that by using a cannula assembly kit of the invention a surgeon can obtain a very good or even excellent determination and/or visibility of the position of a surgical instrument relative to the surgical site or a point or area at the surgical site, which thereby results in an increased control of the instrument, which both reduce the risk of making mistakes during the surgery and at the same time may reduce the required time for a minimal surgery procedure.

In order to an operator to move a surgical instrument in a relatively gentle way, it is standard to provide a cannula (sometimes also called a sleeve) to provide an access port through the incision. The cannula functions as a portal for the subsequent placement of a surgical instrument, such as graspers, scissors, staplers, etc. Usually the cannula is inserted through the incision by using an obturator which is temporarily inserted through the access port of the cannula. A set comprising an obturator and a cannula is called a trocar. The obturator may be a metal or plastic sharpened or non-bladed tip. Where the obturator comprises a sharp tip, the tip may be used by the operator to make the incision. Where the obturator is of the non-bladed tip type, the operator uses a scalpel to cut through at least a skin top layer where after the trocar can be pressed through the incision. When the trocar has been pressed through the incision, the obturator is removed and the cannula now forms an access port. The cannula usually comprises one or more seals to seal against gas slip-out and to accommodate an instrument.

The cannula assembly kit of the invention advantageously comprises one or more seals e.g. such as the seals described in the article "Trends in Laparoscopy: Sealing Technology" Posted on Medical Device And Diagnostic Industry www.mddionline.com by mddiadmin on Aug. 1, 2009.

The terms distal and proximal should be interpreted in relation to the orientation of the cannula.

The phrase "distal to" means "arranged at a position in distal direction to". The phrase "distally arranged" means arranged distally to the distal end of the surgical instrument.

The term "substantially" should herein be taken to mean that ordinary product variances and tolerances are comprised.

The term "about" is generally used to ensure that what is within measurement uncertainties are include. The term "about" when used in ranges, should herein be taken to mean that what is within measurement uncertainties are included in the range.

The phrase "real time" is herein used to mean the time it requires the computer to receive and process constantly changing data optionally in combination with other data, such as predetermined data, reference data, estimated data which may be non-real time data such as constant data or data changing with a frequency of above 1 minute to return the real time information to the operator. "Real time" may include a short delay, such as up to 5 seconds, preferably within 1 second, more preferably within 0.1 second of an occurrence.

The Term "operator" is used to designate a surgeon or a robotic surgeon i.e. a robot programmed to perform a laparoscopic procedure on a patient.

The term "surgical instrument" means herein a laparoscopic tool comprising a surgical tool adapted for performing surgery onto the tissue within the surgery cavity e.g. a grasper, a suture grasper, a cutter, a sealer, a stapler, a clip applier, a dissector, scissors, shears, a suction instrument, a clamp instrument, an electrode, a coagulation device, a curette, ablators, scalpels, a needle holder, a needle driver, a spatula, forceps, a biopsy and retractor instrument or a combination thereof.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Throughout the description or claims, the singular encompasses the plural unless otherwise specified or required by the context.

In an embodiment the cannula assembly kit of the invention is adapted to constitute a part of a trocar suitable for use in minimally invasive surgery. The cannula assembly kit comprises a cannula and a pattern generating member. The cannula has a distal end and a proximal end and comprises an elongate cannula shaft portion extending from the proximal end to the distal end and an access port through said elongate cannula shaft portion, such that a surgical tool of a surgical instrument can be inserted through the access port.

Advantageously the cannula assembly kit comprises a flange portion at its proximal end for holding the cannula assembly kit in position after it has been inserted through an incision.

In use the distal end of the cannula shaft portion is inserted through the incision e.g. together with a distal end of an obturator and the proximal end optionally comprising a flange portion remains outside the incision to ensure a safe positioning of the cannula. The flange portion may have any shape or size. The cannula shaft portion may have any cross-sectional shapes e.g. round, oval or angular for example as the cross-sectional shapes of prior art cannulas.

In the following the cannula assembly kit is described with a flange portion at its proximal end, however it should be understood that such flange portion may be omitted, in particular where the cannula assembly kit is part of or adapted to be handled by a robot as described below.

The pattern generating member comprises a pattern light source and a projector, wherein the pattern light source is operatively connected to the projector for projecting a light pattern. At least the projector of the pattern generating member is configured to be at least temporarily fixed to the cannula shaft portion of said cannula. Preferably at least the projector of the pattern generating member is configured to be fixed to the cannula shaft portion of said cannula to form a substantially rigid connection between said projector and said cannula shaft portion.

The term "access port" means a port through which a surgical instrument can be inserted. The access port may comprise a seal or an insulation, a lid and/or similar which fully or partly locks or fills out the access port when the surgical instrument is not inserted in the access port. The seal, insulation and/or seal ensure that undesired amounts of gasses do not escape and deflate the body cavity. When a surgical instrument is not inserted in the access port, the seal or the insulation advantageously seals against undesired outslip of gas.

The term "rigid connection" means a connection which ensures that the relative position between rigidly connected elements is substantially constant during normal use.

Although the assembly kits of the invention are mainly described in an unassembled state, the invention should be interpreted to also include the assembled corresponding version(s) of the assembly kits.

In use the projector will be moved in a correlated way with at least some of the movement of a surgical instrument inserted through the access port of the cannula shaft portion and thereby images of the projected light pattern from the projector will change, thereby providing the operator with visual information about the position of the surgical instrument relative to the surgical site.

Advantageously at least the projector of the pattern generating member is configured to be at least temporarily fixed to the cannula shaft portion of the cannula, such that any lateral movement of a surgical tool of a surgical instrument inserted through the access port results in a correlated movement of the projector and thereby a correlated change of the reflections of the projected light pattern which can be imaged onto a screen via a camera e.g. of a scope, such as an endoscope. The change of the reflected pattern is herein also referred to as the recorded or recordable pattern.

The phrase "a correlated change" or "a correlated movement" means a change or movement which corresponds to the lateral movements of the surgical instrument such that a given lateral movement of the surgical instrument results in a given and/or corresponding change or movement of respectively the projected light pattern and the projector. In an embodiment the movement of the surgical instrument may result in a gearing of the change or movement of respectively the projected light pattern and the projector. A change of the projected light pattern is herein used to mean a change of reflections of the projected light seen on a surface arranged distal to the cannula.

The pattern will reach an inner wall of a body cavity in which the minimally invasive surgery is performed—herein also referred to as the surgical site.

The surgical site often comprises a very curved and uneven surface, which will be visible from the shape of the pattern as it is reflected on the surgical site. The projector will project the light pattern on an area of the surgical site such that the contours and/or the topography of the surgical site and the position of the surgical instrument can be deduced by the operator based on indirect vision of the light pattern.

The surgical site may comprise one or more sensitive point or areas which advantageously may be protected against damage, such a one or more veins and/or nerves. By using an embodiment of the cannula assembly kit, the surgeon may ensure that such sensitive point or areas are not accidently damaged by a surgical instrument inserted in to the access port of the cannula.

In an embodiment at least the projector of the pattern generating member is configured to be at least temporarily fixed to the cannula shaft portion of the cannula, such that any tilting movements of the cannula result in a correlated movement of the projector and thereby a correlated change of the reflections of the projected light pattern. In an embodiment the reflections of the projected light pattern is received by a camera. The camera may in an embodiment be mounted to or form part of the cannula. The camera may optionally be mounted at the distal end of the cannula arranged for monitoring reflected light. By having the camera fixed to the cannula or integrated with the cannula any risk of damaging tissue by the camera may be reduced. Further the camera need not be held by the operator or an assisting operator. In an embodiment the camera is mounted to be pivotally moved relative to the shaft portion of the cannula. Thereby the operator can angle the camera in any desired direction.

In an embodiment the camera is mounted to a scope, such as an endoscope. The camera may transmit the recorded signal to a screen and/or transmit the recorded signal to a robot configured for maneuvering the surgical instrument. In an embodiment the camera forms part of a robot configured for maneuvering the surgical instrument. The recorded signal may preferably be transmitted in real life speed to ensure that the time delay becomes as small as possibly.

In an embodiment the camera is configured for transmitting the recorded signal in real life to a screen which is visible to a surgeon or an observer of the minimally invasive surgery.

In an embodiment the projector of the pattern generating member is configured to be at least temporarily fixed to the cannula shaft portion of the cannula such that at least a portion of the light pattern is projected in a distal direction.

Distal direction means herein in a direction, which is parallel with or up to 90 degrees in any direction relative to a center axis of the access port or—where the center axis is not straight—relative to tangent to the center axis at the access port exit. In an embodiment the term "distal direction is used to mean a direction, which is parallel with or up to 90 degrees in any direction relative to a center axis of the access port or—where the center axis is not straight—relative to tangent to the center axis at the access port exit. Advantageously at least a portion of the light pattern is projected in a direction which is parallel with or up to 30 degree relative to a direction parallel with the center axis of the access port or relative to tangent to the center axis of the access port at the access port exit and preferably at least a portion of the light pattern is projected in a direction which is parallel with or up to 15 degree relative to a direction parallel with the center axis of the access port or tangent to the center axis at the access port exit, such as up to 10 degree relative to a direction parallel with the center axis of the access port or tangent to the center axis at the access port exit.

The access port exit is the exit of the access port at the distal end of the cannula shaft portion.

As it will be further explained below, in an embodiment the cannula is bendable and/or bent and in such situations the distal direction should be determined in respect to the distal end of the cannula. For certain surgical procedures it is desired that the cannula is bent or bendable to a very high degree e.g. up to 180 degrees, such as up to about 90 degrees. The distal direction is determined as the direction parallel to tangent to the center axis of the access port at the access port exit ±up to 45 degrees, such as ±up to 30 degrees, such as ±up to 15 degrees. Where the cannula is bendable and/or bent and at the same time straight in an end section comprising the access port exit, the tangent to the center axis of the access port at the access port exit is identical to the center axis at the end section comprising the access port exit.

In an embodiment the projector of the pattern generating member is configured to at least temporarily fixed to the cannula shaft portion of the cannula such that at least a portion of the light pattern is projected in a proximal direction, such as in a direction opposite to a distal direction. This embodiment is in particular advantageous where the target of the surgical site is laterally positioned relative to a surgical instrument inserted through the access port.

In an embodiment the projector of the pattern generating member is configured to be at least temporarily fixed at the distal end of the cannula shaft portion.

Advantageously the distal end of the cannula shaft portion has a distal access port exit and comprises an end edge in the vicinity of the distal access port exit. The end edge optionally frames the distal access port exit. The projector of the pattern generating member is configured to be at least temporarily fixed at the end edge, preferably to form a rigid connection thereto. The projector is preferably arranged for projecting the light pattern in a distal direction, preferably such that at least a portion of the light pattern is projected in a direction which is parallel with or up to 45 degrees relative to a direction parallel with the center axis of the access port. In an embodiment the projector is arranged for projecting the light pattern in a distal direction, which is parallel with or up 30 degrees relative to a direction parallel with the center axis of the access port, such as in a direction which is parallel with or up to 15 degrees relative to a direction parallel with the center axis of the access port, such as in a direction which is parallel with or up to 10 degrees relative to a direction parallel with the center axis of the access port.

In an embodiment at least a portion of the light pattern is projected in a direction which is parallel with or up to 45 degrees relative to a direction parallel with tangent to the center axis of the access port at the access port exit. In an embodiment the projector is arranged for projecting the light pattern in a distal direction, which is parallel with or up 30 degrees relative to tangent to the center axis of the access port at the access port exit, such as in a direction which is parallel with or up to 15 degrees relative to tangent to the center axis of the access port at the access port exit, such as in a direction which is parallel with or up to 10 degrees relative to tangent to the center axis of the access port at the access port exit.

The end edge is advantageously an edge extending between an inner surface defining the access port and an outer surface of the cannula shaft portion at the distal end of the cannula shaft portion. In an embodiment the end edge is substantially orthogonal to the center axis of the access port and/or to tangent to the access port at the access port exit. In an embodiment the end edge has an angle of larger than 90 degrees to the center axis and/or to tangent to the access port at the access port exit, such as an angle of from 100 to 125 degrees to the center axis and/or to tangent to the access port at the access port exit.

The cannula assembly kit may comprise several projectors and/or several pattern generating members.

In an embodiment the pattern generating member comprises two or more projectors wherein the pattern light source is operatively connected to the projectors for projecting light patterns. At least the projectors of the pattern generating member are configured to be at least temporarily fixed to the cannula shaft portion of the cannula, preferably at a distance from each other, such as at the end edge at diagonal sides of the distal access port exit.

The pattern light source may comprise a splitter and/or a filter splitting and or filtering the light into two or more fractions for said respective projectors, where said two or more light portions may be equal or different e.g. with respect to power, wavelengths, wavelength profiles. The two or more projectors may be equal or different from each other e.g. with respect to pattern shape or size.

In an embodiment the cannula assembly kit comprises two or more pattern generating members. The two or more pattern generating members may be equal or different from each other e.g. with respect to power, wavelengths, wavelength profiles pattern shape or size.

In an embodiment the cannula shaft portion comprises an access section adapted to be inserted through a surgical incision for allowing a surgical instrument to be inserted through the access port, wherein the access section is at least partially rigid, preferably the entire access section of the cannula shaft portion or the entire cannula shaft portion is substantially rigid. The rigidity of the cannula shaft portion ensures that when the cannula shaft portion is subjected to a tilting movement—e.g. by tilting of an instrument inserted into the access port—the projector will be moved in a correlated way and thereby resulting in a correlated change of the reflections of the projected light pattern which can be imaged onto a screen or transmitted to a robot via a camera e.g. mounted to or integrated with the cannula and/or a camera of a scope.

The recorded signal may preferably be transmitted in real time speed to ensure that the time delay becomes as small as possibly.

The term "access section" is used to denote the length section of the cannula shaft portion, which is adapted to be fully or partly inserted into the incision. It should be noted that a rigid section may comprise one or more layers, e.g. seals of non-rigid material.

In an embodiment at least said access section is collapsible by comprising a seal and or an isolation which collapses when the access port is free of an inserted instrument, to thereby prevent gas escape via the access port and thus prevent deflation of the abdominal or other surgical cavity inside the patient.

In an embodiment at least the access section is collapsible by being of a collapsible material, such at least at the access section is at least partly collapsed when the access port is free of an inserted instrument.

In an embodiment the cannula shaft portion comprises an access section adapted to be inserted through a surgical incision for allowing a surgical instrument to be inserted through the access port, wherein the access section is collapsible. Advantageously at least the access section of the cannula shaft portion is of a non-rigid material, such as an elastomer e.g. rubber.

The rigidity is determined at 25° C.

In principle the cannula shaft portion may be straight or bent. Where the cannula shaft portion is substantially rigid, it is desired that the cannula shaft portion is relatively straight or optionally bent in a relatively soft curve.

Where the cannula shaft portion is straight, the access port will usually be straight as well.

In an embodiment the pattern generating member is detachable from the cannula shaft portion.

Preferably at least the projector of the pattern generating member is configured to be temporarily fixed to the cannula shaft portion by a click lock, a sleeve lock, a screw lock, a turn lock, a wedge lock or combinations thereof.

Advantageously the pattern light source is not fixed or adapted to be fixed to the cannula shaft portion. In an embodiment the pattern light source is fixed or adapted to be fixed to the flange portion of the cannula. The operative connection can in principle be any kind of wave guiding element or elements, such as an optical fiber, one or more lenses, mirrors, splitters, collimators, amplifiers or any other suitable optical element. The optical connection between the pattern light source and the projector is preferably provided by an optical fiber.

Where only the projector is mounted to the cannula shaft portion, the remaining part of the pattern generating member including the pattern light source may be reused without requiring sterilization.

In an embodiment at least the projector and the pattern light source of the pattern generating member are temporarily fixed to the cannula by a sleeve.

In an embodiment all elements of the pattern generating member are temporarily fixed to the sleeve. The elements of the pattern generating member comprise the projector and the pattern light source and optional power source and/or one or more controlling elements such as the pattern light source control unit described below.

In an embodiment at least the projector of the pattern generating member is permanently fixed to the cannula.

In an embodiment the pattern light source and an optional battery are fixed or adapted to be fixed to the cannula shaft portion.

In an embodiment the pattern light source and an optional battery are arranged in an external light source unit and are optically connected to the projector e.g. via an optical fiber, directly connected or by use of free space optics.

In an embodiment the pattern light source is adapted to be arranged at a distance to the projector, the pattern light source is preferably incorporated into a pattern light source housing arranged to be positioned at a distance to the cannula and advantageously connected to the projector via connection means comprising an optical fiber, preferably the optical fiber is protected by a polymer cover.

In an embodiment at least the projector of the pattern generating member is incorporated in or mounted to a sleeve. The sleeve preferably comprises a sleeve end edge portion comprising the projector. The sleeve is configured to be mounted onto the cannula shaft portion. Optionally the sleeve constitutes an outer and/or an inner seal for minimizing undesired gas leak. The sleeve is advantageously fixed or fixable to the flange portion. In an embodiment the pattern light source is incorporated in or mounted to a sleeve at its proximal end where the sleeve is mounted to the flange portion.

The sleeve may comprise any material including polymer material and/or metal. Preferably the sleeve has an outer surface which is hydrophilic and advantageously has a low friction. In an embodiment the sleeve comprises a coating for reducing friction e.g. a coating of PTFE or parylene. In an embodiment the surface of the sleeve has been subjected to a plasma treatment and/or chlorination.

Advantageously the sleeve is of elastomer, such as one more thermoplastic elastomers, rubber and/or silicone. Preferred materials comprise polyisoprene, silicone, butyl-ethylene propylene (diene) polymer and/or styrene butadiene rubber.

In an embodiment the cannula comprises a mounting through hole for mounting the projector, preferably the mounting through hole extends through the cannula shaft portion such that the projector can be mounted at or adjacent to the distal end of the cannula shaft portion. Thereby the projector can be mounted via said mounting through hole after the cannula has been inserted through a surgical incision.

In an embodiment the sleeve comprises a mounting through hole for mounting the projector prior to or after the cannula has been inserted through a surgical incision.

In an embodiment at least the projector of the pattern generating member is permanently fixed to the cannula shaft portion, preferably the projector is integrated with the cannula to form an integrated cannula assembly.

The pattern light source can in principle be any kind of light source capable of providing a desired pattern. The light source may be a coherent light source or an incoherent light source.

The term "coherent light" is herein used to denote laser light whereas "incoherent light" includes any non-laser light irrespectively of its degree of coherence. Incoherent light with a relatively high degree of coherence (sometimes called partially coherent light) is often preferred because the coherent light provides a highly bright pattern, while the incoherent light source generally can be obtained at a much lower cost than coherent light.

In an embodiment the pattern light source is a coherent light source, such as a semiconductor light source, such as a laser diode and/or a VCSEL light source.

In an embodiment the pattern light source is an incoherent light source, preferably the light source is a semiconductor light source, such as a light emitting diode (LED).

Advantageously, the light pattern is generated by at least one laser and/or LED. Lasers and LEDs (light emitting diodes) are advantageous as they can generate light patterns that are well defined and it is possible to choose the wavelength and thus color such that the pattern is enhanced in the remote vision, for example such that the light pattern is clearly visible and enhanced on the monitor and/or easily detectable for computer recognition, decoding and/or vision procession.

The pattern light source advantageously has a relatively narrow band width thereby providing a bright light in the narrow bandwidth, while simultaneously emitting a relatively low light energy. It is advantageous both to avoid undesired heating of the surgical target site and simultaneously have low risk of blinding and/or result in undesired side or error reflections which may distort the recording by the camera.

In an embodiment the pattern light source has a band width (full width at half maximum—FWHM) of up to about 50 nm, such as from 1 nm to about 40 nm. Preferably the narrow band width of the pattern light source is about 25 nm or less, such as about 10 nm or less.

In an embodiment the pattern light source is a broad band light source such as a supercontinuum light source e.g. spanning at least an octave within the bandwidth range from 400 nm to 2600 nm. Above 2600 nm light transmitted in a silica fiber will be strongly attenuated.

In an embodiment the pattern light source is configured for emitting at least one electromagnetic wavelength within the UV range of from about 10 nm to about 400 nm, such as from about 200 to about 400 nm.

In an embodiment the pattern light source is configured for emitting at least one electromagnetic wavelength within the visible range of from about 400 nm to about 700 nm, such as from about 500 to about 600 nm.

In an embodiment the pattern light source is configured for emitting at least one electromagnetic wavelength within the IR range of from about 700 nm to about 1 mm, such as from about 800 to about 2500 nm.

In an embodiment the pattern light source is configured for emitting two or more distinguished wavelengths or wavelength bandwidths and advantageously the pattern light source is configured for switching between said distinguished wavelengths or wavelength bandwidths.

Light in the lower wavelengths e.g. below 600 nm requires relatively high power in order to be visually distinguished from illuminating light emitted to light up the area under surgery—usually emitted from a scope, such as an endoscope.

In an embodiment the pattern light source comprises at least one wavelength within the visible range.

In an embodiment the pattern light source comprises at least one wavelength within the invisible range, such as the UV or the IR range. Where the pattern light source comprises wavelengths in the invisible range, such wavelengths are advantageously detected by the camera system and converted to a visible wavelength for displaying to the operator e.g. by digital processing.

In an embodiment the pattern generating member comprises two or more pattern light sources having equal or different bandwidths, wherein the two or more pattern light sources preferably are operatively connected to the projector.

the two or more pattern light sources can be operated independently of each other i.e. they can independently be switched on and off e.g. using a non-hand held unit or by a unit incorporated into the flange portion.

In an embodiment the two or more pattern light sources can be connected to separate projectors.

Generally it is desired that the pattern light source (or sources) can be switched on and off and optionally be modified in wavelengths and/or intensity, using a pattern light source control unit. In an embodiment the pattern light source control unit is a non-hand held unit, such as a pedal or a voice activated control unit—thereby in a simple manner the operator can control the light pattern. In an embodiment the pattern light source control unit is incorporated into the flange portion.

In an embodiment the pattern light source (or sources) is controlled by a robot—e.g. by being part of the robot. The pattern light source control unit may advantageously be computer controlled.

Advantageously the pattern light source is arranged to provide a pattern output power which is sufficient to generate a visible pattern, but not too high such that an undesired amount of heat may be generated. Preferably the pattern light source is arranged to provide a pattern output power up to about 100 mW such as at least about 0.1 mW, such as from about 1 to about 100 mW, such as from about 3 my to about 50 mW. Preferably the pattern output power is adjustable. The pattern output power is determined as the output power of the projector.

Advantageously the pattern light source is tunable in wavelength and/or power and the cannula assembly kit comprises a regulator for tuning the pattern light source, preferably such that movements of a surgical instrument inserted through the access port trigger the regulator to a coordinated tuning of the pattern generating member. The tuning is advantageously performed such that movements in the distal towards proximal direction or vice versa of a surgical instrument inserted through the access port trigger the regulator to a coordinated tuning of the pattern generating member. In an embodiment the regulator is a tunable button arranged at an inner wall of the cannula shaft portion such that movement of a surgical instrument in the distal towards proximal direction or vice versa tunes the light intensity of the pattern light source up and down and/or changes the wavelengths of the pattern light source. In an embodiment where the pattern light source (or sources) is controlled by a robot the robot may advantageously control or comprise the surgical instrument inserted through the access port and the regulator for tuning the pattern light source may advantageously also be part of or at least controlled by the robot.

Advantageously the projector of the pattern generating member comprises a phase optic element, a spatial light modulator, a multi-order diffractive lens, a holographic lens, a mirror arrangement, a computer regulated optical element, and/or a computer regulated mechanically optical element e.g. a mems (micro-electro-mechanical) element.

The phase optic element may advantageously be a diffractive optic element (DOE).

In an embodiment the phase optics element is capable of producing an image having periodic intensity distribution.

Diffractive optic elements are well known in the art and may for example utilize a surface with a complex micro-structure for its optical function. The micro-structured surface relief profile has two or more surface levels. The surface structures are either etched in fused silica or other glass types, or embossed in various polymer materials. Additionally, diffractive optics can realize almost the same optical functions as refractive optics such as lenses, prisms or aspheres, but they are much smaller and lighter. DOEs are not limited to laser applications; partially coherent light from LEDs or other light sources can also be modulated.

In an embodiment the DOE is as described in US 2013/0038836 e.g. as shown in FIG. 1 and/or as described in section [0015] of US 2013/0038836.

In an embodiment the diffractive optic elements comprise a "multi-order diffractive" lens, such as a conventional diffractive-optic lens utilizing a single diffraction order in which the optical power of the lens is directly proportional to the wavelength of light.

The projector may comprise any type of beam manipulating element for providing the desired pattern e.g. one or more lenses and/or mirrors and/or splitters and/or filters and/or collimators.

In an embodiment the projector comprises a spatial light modulator. The spatial light modulator is configured for modulating the light pattern for example by modulating the transparency of a pattern cover e.g. by a computer modulation. In an embodiment the spatial light modulator is arranged for modulating the intensity and/or the phase of the light from the pattern light source to thereby modulate the emitted light pattern.

In order to ensure that the cannula can be inserted through a desired small incision it is generally desired that the part of the pattern generating member to be mounted to the cannula shaft portion prior to insertion into an incision is relatively small.

Advantageously the projector of the pattern generating member has a maximally extending area perpendicular to the center axis of the access port when the pattern generating member is fixed to the cannula shaft portion, which maximally extending area is up to about 8 cm2, such as up to about 4 cm2, such as up to about 2 cm2, such as from about 0.01 to about 1 cm2, such as from about 0.1 to about 0.5 cm2. Preferably the projector of the pattern generating member is configured to be at least temporarily fixed at the end edge in the vicinity of the distal access port exit and the projector is preferably shaped such that the projector does not extend laterally beyond the end edge or up to 5 mm laterally beyond the end edge.

In an embodiment the projector of the pattern generating member has a projector face from where the light is to be emitted and the projector is pivotable, so it can be pivotally unfolded from a first folded position where the projector face is not facing in the distal direction to a second position where the projector face is facing in the distal direction. Thereby the cannula can be inserted into an incision when the projector is in a first folded position and there after the projector can be unfolded to its second position. Optionally the unfolding can be provided by triggering a release button at the inner wall of the cannula shaft portion e.g. by the surgical instrument—e.g. by a tilting of the surgical instrument—after the cannula has been inserted through the incision such that the projector is unfolded to its second position e.g. by a spring mechanism.

The pattern may have any desired shape.

In an embodiment the projector is fixed or adapted to be fixed to the cannula shaft portion such that the pattern remains substantially stationary when the surgical instrument is subjected exclusively to a circumferential movement with the longitudinal axis of the surgical instrument.

In an embodiment the projector when fixed to the cannula shaft portion is configured to emitting a pattern, which pattern when projected to a surface orthogonal to the center axis of the access port has at most 10 fold rotational symmetry, preferably the pattern has at most 8 fold rotational symmetry.

Such pattern which is not fully rotational symmetrical but has up to 10 fold rotational symmetry gives the user an even better visual information about the position of the surgical instrument relative to the surgical site.

In an embodiment the projector of the pattern generating member is configured to emit a pattern comprising an arch shape, ring or semi-ring shaped lines, a plurality of angled lines and/or a coded structured light configuration. In an embodiment the pattern comprises a grid of lines, e.g. a crosshatched pattern optionally comprising substantially parallel lines when emitted to a planar surface.

The changes in the grid lines due to lateral movements of the surgical instrument can for example be used to deduce the contours of the body cavity such as projected surface and/or the contours and/or topographic shape of the surgical field. The changes in the angle and distance between crossing and/or parallel grid lines during movement(s) of the surgical instrument can for example be used to determine the orientation of the surgical instrument.

The phrases "surgical field", "surgical site" and "surgery target site" are herein used interchangeably.

In an embodiment the light pattern comprises a plurality of light dots. When the surgical instrument is moved, the position and/or the distance between the dots will change, which enhances the operator's ability even further to deduce the position of the surgical instrument and the area contours of the surgical field.

In an embodiment of the pattern generating member is configured to emit a pattern comprising a coded structured light configuration comprising a plurality of light dots with different shapes and/or sizes arranged in a preselected configuration. The pattern comprising a coded structured light configuration is in particular suitable for determining a topographic shape of the target surface.

Patterns comprising coded structured light configurations are for example described in "Pattern codification strategies in structured light systems" by Salvi et al. Pattern Recognition, Volume 37, Issue 4, April 2004, Pages 827-849.

In an embodiment the projector fixed to the cannula shaft portion is configured to emit a pattern which pattern, when projected to a surface perpendicular to the longitudinal axis of the body portion of the surgical instrument, comprises a plurality of angled lines. Advantageously the pattern comprises a grid of lines, such as a grid comprising one or more sets of parallel lines.

Where the pattern has an angled lines when projected to a surface orthogonal to the center axis of the access port, a tilting of the surgical instrument inserted into the access port can for example be observed by a change of such angled lines e.g. by a deformation of one or more of the lines, by change of line angles and/or by change of distance between lines.

The pattern is advantageously sufficiently large to ensure good visual perception of the surgical instrument and movement thereof.

At the same time, since the projector is fixed to the cannula shaft portion the risk of direct contact between the projector and tissue during surgery is relatively small and it has been found that for most procedures the projector requires less cleaning during minimally invasive surgery than an endoscope.

In an embodiment the projector of the pattern generating member is configured to emit a pattern, which pattern when emitted towards a plane surface at a distance of about 80 mm from the distal end of the cannula shaft portion and normal to a center axis of the cannula shaft portion, has a grid area of up to about 225 $cm^2$, such as of up to about 100 $cm^2$, such as of up to about 9 $cm^2$.

The flange portion comprises a handle part, the flange portion comprising means for being temporally fixed to an obturator.

In an embodiment the cannula comprises two or more access ports through the flange portion and the cannula shaft portion. Thereby several surgical instruments can be inserted simultaneously.

In an embodiment the cannula comprises two or more cannula shaft portions and an access ports through the flange portion and the cannula shaft portions suitable for inserting a surgical instrument through each of the respective access ports.

In an embodiment the cannula assembly kit comprises a cleaning element for cleaning the projector. In an embodiment the cleaning element is in the form of a wiping element arranged for wiping and/or washing the projector. In an embodiment the cleaning element is in the form of a spray element arranged for spraying and/or blowing the projector with a fluid such as gas or liquid. An example of a suitable cleaning element is as the cleaning device described in U.S. Pat. No. 8,397,335.

In an embodiment the cannula is adapted for being handled by a surgeon—i.e. to be mounted in an incision of a patient to provide the access port to the surgical site.

In an embodiment the cannula is adapted for being maneuvered by a robot—i.e. to be mounted in an incision of a patient using a robot to provide the access port to the surgical site.

In an embodiment the cannula is a part of the robot.

In an embodiment the invention also comprises a trocar assembly kit for use in minimally invasive surgery. The trocar assembly kit comprises a cannula assembly as described above and an obturator. The obturator may in principle be any kind of obturator configured to be used with a cannula.

The obturator has a distal end and a proximal end and comprises a head portion at its proximal end, a tip portion at its distal end and a rigid obturator shaft portion extending between the head portion and the tip portion, wherein the cannula and the obturator are correlated to each other such that the tip portion of the obturator can be instead through the access port of the cannula and the head portion of the obturator can be temporally fixed to the flange portion of the cannula, preferably such that a seal is formed in the access opening between the cannula and the obturator.

Advantageously the obturator comprises a projector protection arrangement correlated with the projector of the cannula assembly kit to at least partly cover the projector when the cannula assembly kit and the obturator are in an assembled state. Thereby the projector can be protected by the projector protection arrangement during insertion of the trocar assembly through an incision. The projector protection arrangement is advantageously arranged to be at least partly passed into a cavity of the obturator upon withdrawing of the obturator from said cannula access port.

The cannula assembly kit and the obturator are in an assembled state when the tip portion of the obturator is inserted substantially fully through the access port of the cannula shaft portion, and the cannula assembly kit and the obturator are disassembled upon withdrawing of the obturator from said cannula access port.

In an embodiment the projector protection arrangement is arranged to be pivotally folded from a first position where it, at least partly covers the projector to a second position where it at least partly is passed into a cavity of the obturator. The folding from the second position to the first position may for example be performed manually after having inserted the tip portion of the obturator substantially fully through the access port of the cannula shaft portion and the folding from the first position to the second position may for example be performed simply by withdrawing the obturator from the access port and/or by releasing a holding mechanism temporarily holding the projector protection arrangement in the first position.

In an embodiment the projector protection arrangement is arranged to be radially displaced from a first position where it, at least partly covers the projector to a second position where it at least partly is passed into a cavity of the obturator. The radial displacement may for example be provided by a spring arrangement and/or a holding mechanism temporarily holding the projector protection arrangement in one of the first position and the second positions.

In an embodiment the invention also comprises a sleeve assembly suitable for a cannula assembly kit as described above. The sleeve assembly comprises a sleeve and a pattern generating member. The pattern generating member comprises a pattern light source and a projector, wherein the pattern light source is operatively connected to the projector for projecting a light pattern. At least the projector of the pattern generating member is configured to be at least temporarily and rigidly fixed to the sleeve, the sleeve preferably comprises a sleeve end edge portion comprising the projector.

The sleeve may advantageously be as described above.

In an embodiment the sleeve is configured to substantially fully cover at least a cannula shaft portion of a cannula. In an embodiment the sleeve is configured to cover at least a part of a cannula flange portion of the cannula.

In an embodiment the invention also relates to a minimally invasive surgery system comprising a cannula assembly kit preferably as described above, a surgical instrument, a camera and a computer system.

The camera may be a mono camera or a stereo camera. In an embodiment the minimally invasive surgery system comprises two or more camera adapted for recording image data. The minimally invasive surgery system may be configured to combining or multiplexing said image data.

In an embodiment the camera is mounted to or integrated with the cannula e.g. as described above.

The camera may advantageously comprise a charge-coupled device (CDD) image sensor, or a complementary metal-oxide-semiconductor (CMOS) image sensor.

In an embodiment the camera is mounted to a scope. A Scope is herein used to mean any suitable scope, such as an endoscope, a laparoscope anarthroscope, a thoracoscope, a gastroscope, a colonoscope, a laryngoscope, a broncoscope, a cystoscope or a combination thereof. In an embodiment the scope is an endoscope. In an embodiment the scope is a laparoscope.

Advantageously the computer is configured for wide baseline operation comprising a wide angle between the camera and the cannula assembly. The angle between the camera and the cannula assembly and in particular the center axis of the projected light pattern may be stationary or variable and the computer may preferably be configured for determining the angle and compensate therefore. The system may e.g. comprise one or more further sensors for determining the angle between the camera and the cannula assembly. The angle between the camera and the cannula assembly and in particular the center axis of the projected light pattern may for example be at least 5 degrees, such as from 10 to 50 degrees, such as from 25 to 45 degrees.

In an embodiment the minimally invasive surgery system comprises two or more cameras, such as at least one camera mounted to or integrated with the cannula and at least one camera mounted to or integrated with a scope.

In an embodiment the computer system is programmed to determining a spatially position and orientation of the projector. This may for example be performed by ensuring that the project pattern is a coded pattern e.g. an asymmetrical pattern where different areas of the projected pattern seen in cross sectional view may be uniquely identified to determine a spatially position and orientation of the projector.

The minimally invasive surgery system may further comprise one or more illuminating element, such as an illuminating element mounted to or integrated with the scope.

The minimally invasive surgery system may additionally comprise one or more sensors which may be used in the generation of minimally invasive surgery data and/or performing a minimally invasive surgery. Such one or more sensors may include light emitting based sensors, mechanical sensors, electrical sensors and etc. In an embodiment the one or more sensors comprises position tracking sensor(s), accelerometer(s), gyroscope(s) and/or other motion-sensing devices.

It is advantageous that the projected light pattern of the cannula assembly kit comprises at least one wavelength not comprised by the optional other illuminating light sources and/or sensor light sources.

The surgical instrument of the minimally invasive surgery system is advantageously selected from a grasper, a suture grasper, a cutter, a sealer, a stapler, a clip applier, a dissector, scissors, shears, a suction instrument, a clamp instrument, an electrode, a coagulation device, a curette, ablators, scalpels, a needle holder, a needle driver, a spatula, forceps, a biopsy and retractor instrument or a combination thereof.

The computer system may comprise hardware and software for collecting minimally invasive surgery data and/or for performing minimally invasive surgery.

The computer system may comprise one or more hardware elements which are or are adapted to be in data communication.

In an embodiment the computer system is in data communication with the camera to receive image data from the camera. The computer system is programmed to determining real time position data of the surgical instrument, to determining real time topography data of a surface reflecting the light pattern emitted by the cannula assembly kit and/or to determining real time contours of a surface reflecting the light pattern emitted by the cannula assembly kit.

In an embodiment the computer system is configured to transmitting the determined data to a robot, a database and/or a monitor for being displayed.

In an embodiment the surgical instrument forms part of the robot or is adapted for being maneuvered by the robot. The computer system is preferably configured to transmitting the determined data to the robot. In an embodiment the computer system or at least a part of the computer system forms part of the robot.

In an embodiment the cannula assembly kit is adapted for being controlled by a computer or forms part of the computer.

In an embodiment the surgical instrument forms part of a robot or is adapted for being maneuvered by a robot and the computer system is configured for determining a spatially position of the instrument and based at least partly on said real time topography data and said spatially position of the instrument to control the robot to perform movements of the instrument.

In an embodiment the invention also relates to a method of performing a minimal invasive surgery of a target surgical site in an internal body structure below a skin area of a patient. In an embodiment the method comprises, providing an access port to the surgery target site comprising providing an incision through the skin area inserting a cannula assembly kit as described above, inserting a surgical instrument through the access port, inserting a camera element through the access port or through an additional access port to the surgery target site, providing that the projector if the cannula assembly kit is emitting a light pattern, recording image data of the light pattern reflected from the surgery target site by the camera, and moving the surgical instrument for performing the minimal invasive surgery while simultaneously receiving feedback based on the recorded image data.

In an embodiment the method comprises, providing an access port to the surgery target site comprising providing an incision through the skin area inserting a cannula assembly kit with a camera as described above, inserting a surgical instrument through the access port, providing that the projector if the cannula assembly kit is emitting a light pattern, recording image data of the light pattern reflected from the surgery target site by the camera, and moving the surgical instrument for performing the minimal invasive surgery while simultaneously receiving feedback based on the recorded image data.

In an embodiment the method comprising performing the minimally invasive surgery by using the minimally invasive surgery system as described above.

The method of performing a minimal invasive surgery may be performed by an operator i.e. a surgeon and/or a robot.

For example in an embodiment a surgeon is performing an incision and inserting the cannula assembly kit and a robot is performing the remaining method steps.

In an embodiment the entire method of performing a minimal invasive surgery is performed by a robot. The recorded image data may simultaneously be transmitted to a monitor for being displaced such than an observer, such as a supervisor, a surgeon and/or a trainee can observe the minimally invasive surgery performed by the robot.

All features of the inventions including ranges and preferred ranges can be combined in various ways within the scope of the invention, unless there are specific reasons not to combine such features.

BRIEF DESCRIPTION OF EXAMPLES

Preferred embodiments of the invention will be further described with reference to the drawings.

FIG. 1b is a schematic view of an embodiment of an obturator adapted to be used together with the cannula assembly kit of FIG. 1a.

The figures are schematic and are not drawn to scale and may be simplified for clarity. Throughout, the same reference numerals are used for identical or corresponding parts.

Figure 1A:
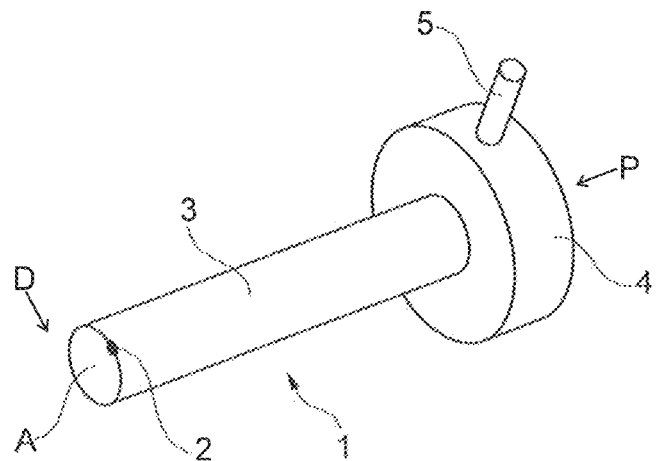
FIG. 1a is a schematic view of an embodiment of a cannula assembly kit.

FIG. 1a illustrates an embodiment of a cannula assembly kit of the invention. The cannula assembly kit comprises a cannula 1 and a pattern generating member wherein only the projector 2 is shown. The cannula has a distal end D and a proximal end P and comprises a flange portion 4 at its proximal end and an elongate cannula shaft portion 3 extending from the flange portion 4 to its distal D end and an access port A through the flange portion 4 and the elongate cannula shaft portion 3, such that a surgical tool of a surgical instrument can be inserted through the access port. The pattern generating member comprises a not shown pattern light source and a projector 2 at least temporarily fixed to the cannula shaft portion 3 of the cannula. The cannula flange portion 4 comprises an insufflation port 5 for insufflating the body cavity.

The obturator and the cannula assembly kit of FIG. 1 are correlated to each other. The obturator 9 shown in FIG. 1b has a distal end D and a proximal end P and comprises a head portion 6 at its proximal end, a tip portion 8 at its distal end and a rigid obturator shaft portion 7 extending between said head portion 6 and said tip portion 8. The tip portion can be bladed or non-bladed.

Figure 1B:
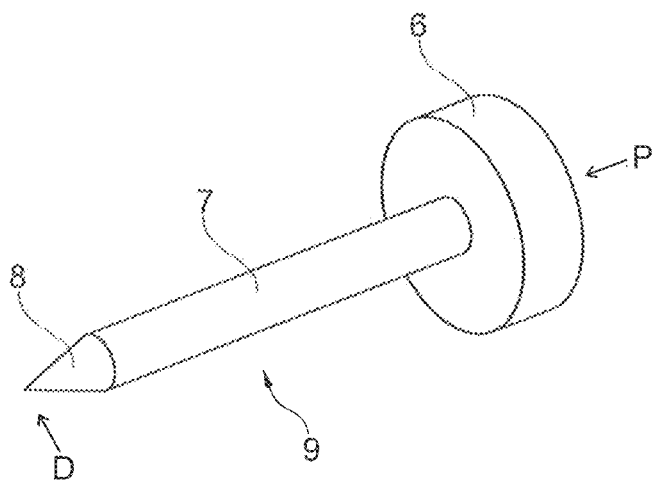
Figure 1C:
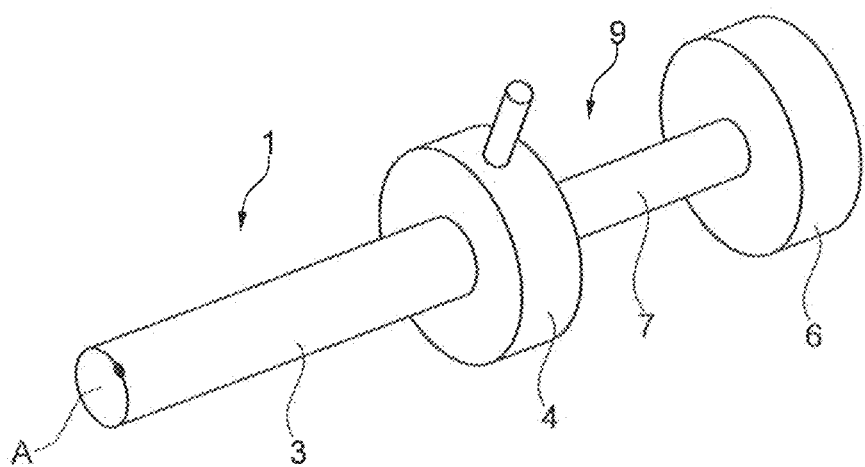
FIG. 1c and FIG. 1d are schematic views of a trocar assembly kit comprising the cannula assembly kit of FIG. 1 and the obturator of FIG. 2 is partly or fully in an assembled state.
Figure 1D:
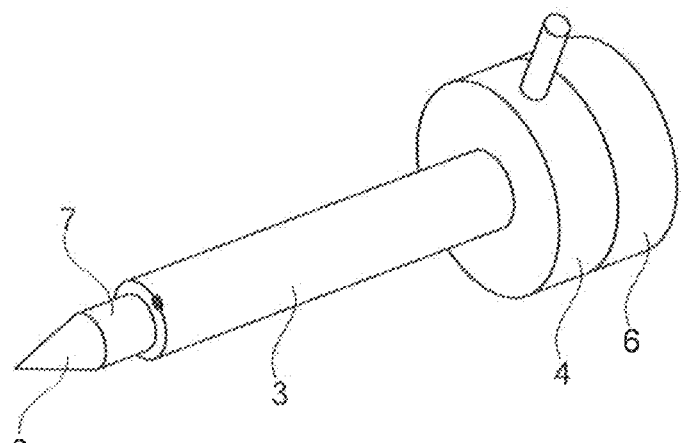

The obturator of FIG. 1b and the cannula assembly kit of FIG. 1 are correlated to each other such that the obturator can be inserted into the access port A of the cannula 1. In FIG. 1c the obturator 9 is partly inserted into the access port A of the cannula 1. In FIG. 1d the obturator 9 is fully inserted into the access port A of the cannula 1 to thereby assemble the trocar assembly kit.

Figure 2:
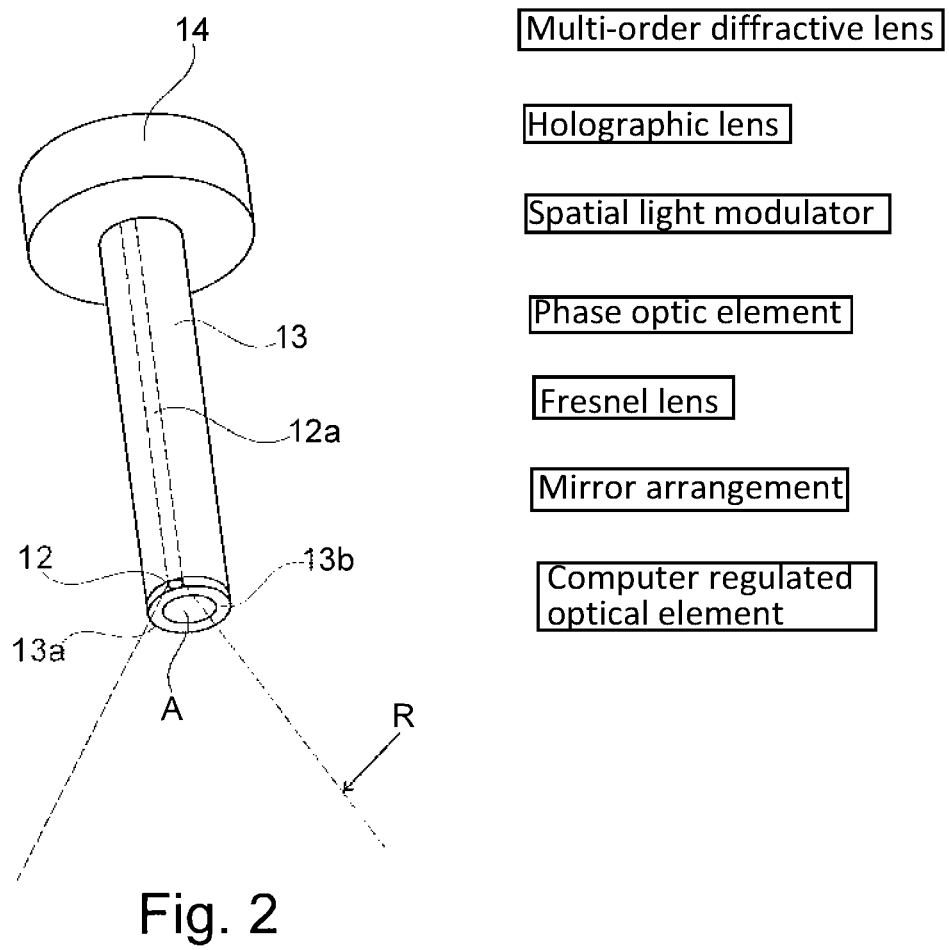
FIG. 2 is a schematic view of an embodiment of a cannula assembly kit, where the shaft portion of the cannula comprises a mounting through hole through which the projector has been mounted.

The cannula assembly kit shown in FIG. 2 comprises a cannula and a pattern generating member wherein only the projector 12 is shown. The cannula comprises a flange portion 14 and an elongate cannula shaft portion 13 extending from the flange portion 14 to its distal end and an access port A. At its distal end the cannula shaft portion 13 has an access port exit 13a and comprises an end edge 13b in the vicinity of said distal access port exit 13a.

The shaft portion 13 of the cannula comprises a mounting through hole 12a indicated on the drawing with dotted lines. The projector 12 has been mounted via the mounting through hole 12a and a not shown optical fiber extends through the mounting through hole 12a for transmitting light to the projector 12.

Figure 3:
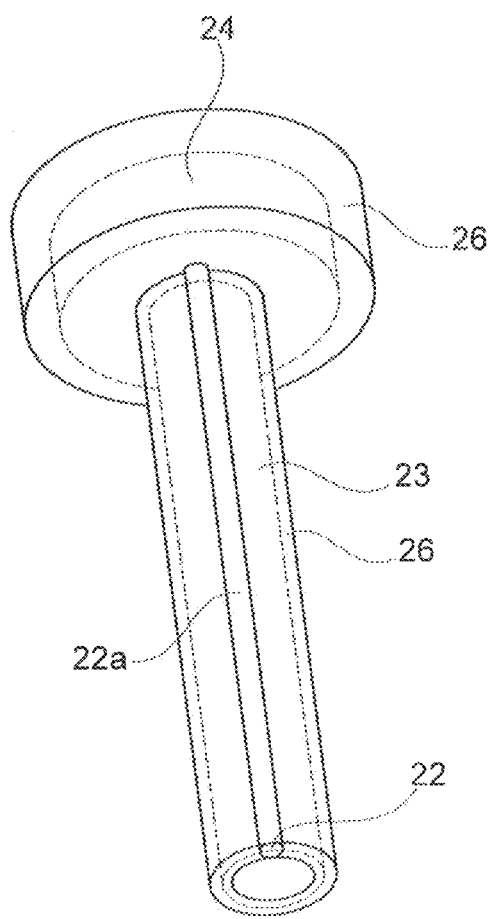
FIG. 3 is a schematic view of an embodiment of a cannula assembly kit comprising a sleeve.

The cannula assembly kit shown in FIG. 3 comprises a cannula and a pattern generating member wherein only the projector 22 is shown. The cannula comprises a flange portion 24 and an elongate cannula shaft portion 23 extending from the flange portion 24 to its distal end and an access port A.

The shaft portion 23 and the flange portion 24 are covered by a sleeve 26 which is mounted to the cannula. The projector 22 is mounted to or integrated in the sleeve 26 and the sleeve also comprises a fiber covering line 22a comprising a not shown optical fiber arranged for transmitting light to the projector 22.

Figure 4:
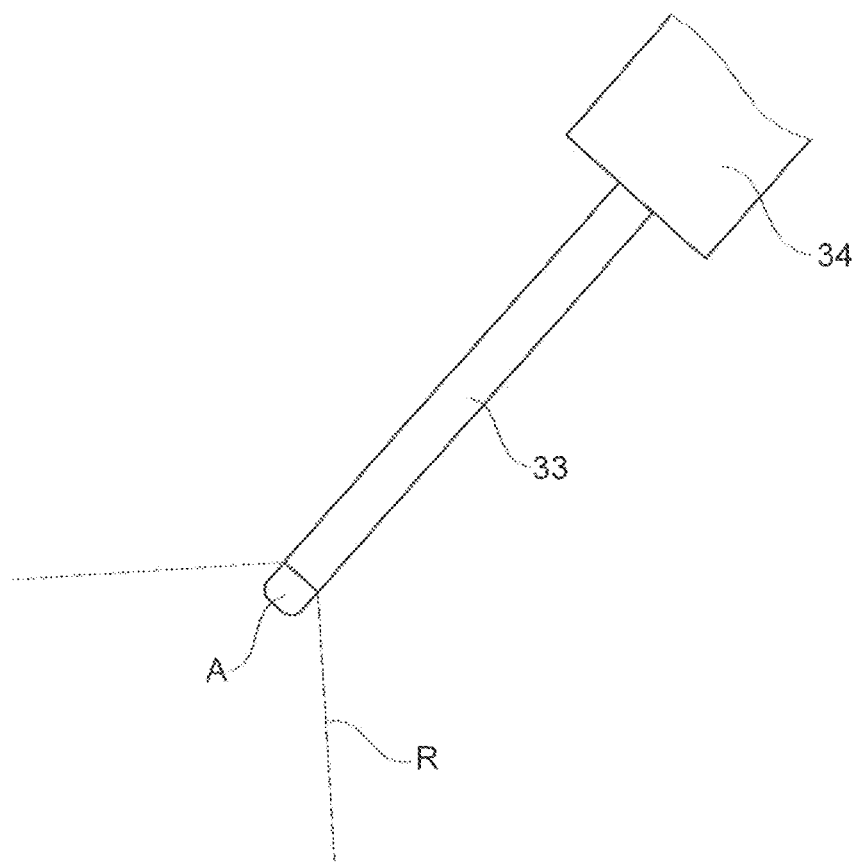
FIG. 4 is a schematic view of an embodiment of a cannula assembly kit with a relatively large flange portion for comprising the pattern light source.

The cannula assembly kits shown in FIG. 4 comprises a flange portion 34 and an elongate cannula shaft portion 33 extending from the flange portion 34 to its distal end and an access port A. The cannula assembly kit also comprises a not shown pattern generating member. The rays R indicate that the not shown projector is positioned at the distal end of the cannula shaft portion 33. The cannula flange portion 34 is relatively large such that a not shown light source and/or battery can be incorporated into the cannula flange portion 34.

Figure 5:
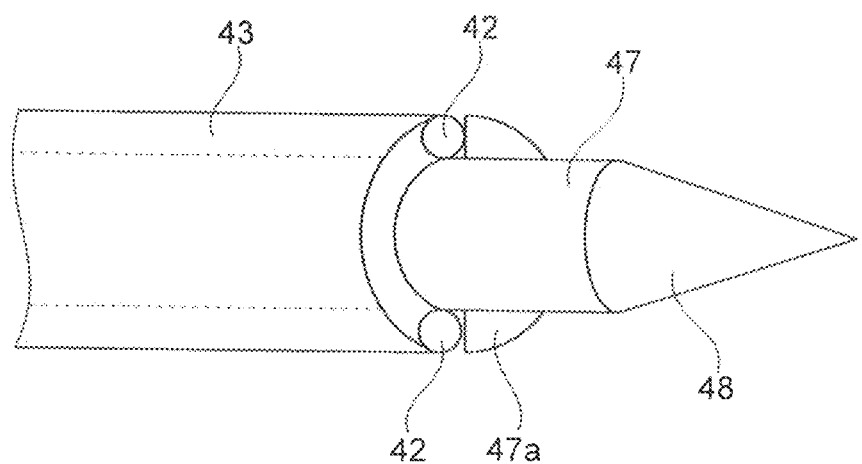
FIG. 5 is a schematic view of a distal end portion of an assembled trocar assembly kit, where the obturator comprises a projector protection arrangement.

The distal end portion of an assembled trocar assembly kit shown in FIG. 5 comprises distal end portions of the correlated cannula assembly kit and obturator. The cannula assembly kit comprises a cannula shaft portion 43 and a projector 42 arranged for projecting a light pattern. The obturator comprises a rigid obturator shaft portion 47 and a tip portion 48. The obturator further comprises a projector protection arrangement 47a correlated with the projector 42 of the cannula assembly kit to at least partly cover the projector 42, such that the projector is at least partly projected during the insertion during surgery. In a not shown modified embodiment the projector protection arrangement is shaped to align with the shape of the tip portion of the obturator such that there will be a more gradually increase of the diameter of the assembled trocar assembly kit from the tip portion of the obturator to the cannula shaft portion of the cannula assembly kit.

When the obturator is withdrawn from the access port of the cannula assembly kit, the projector protection arrangement 47a will at least partly be passed into a cavity of the obturator, such that the projector protection arrangement 47a is not blocking for the withdrawal. The projector protection arrangement 47a may for example be pivotally folded into a cavity of the obturator, by folding towards the tip portion 48.

Figure 6:
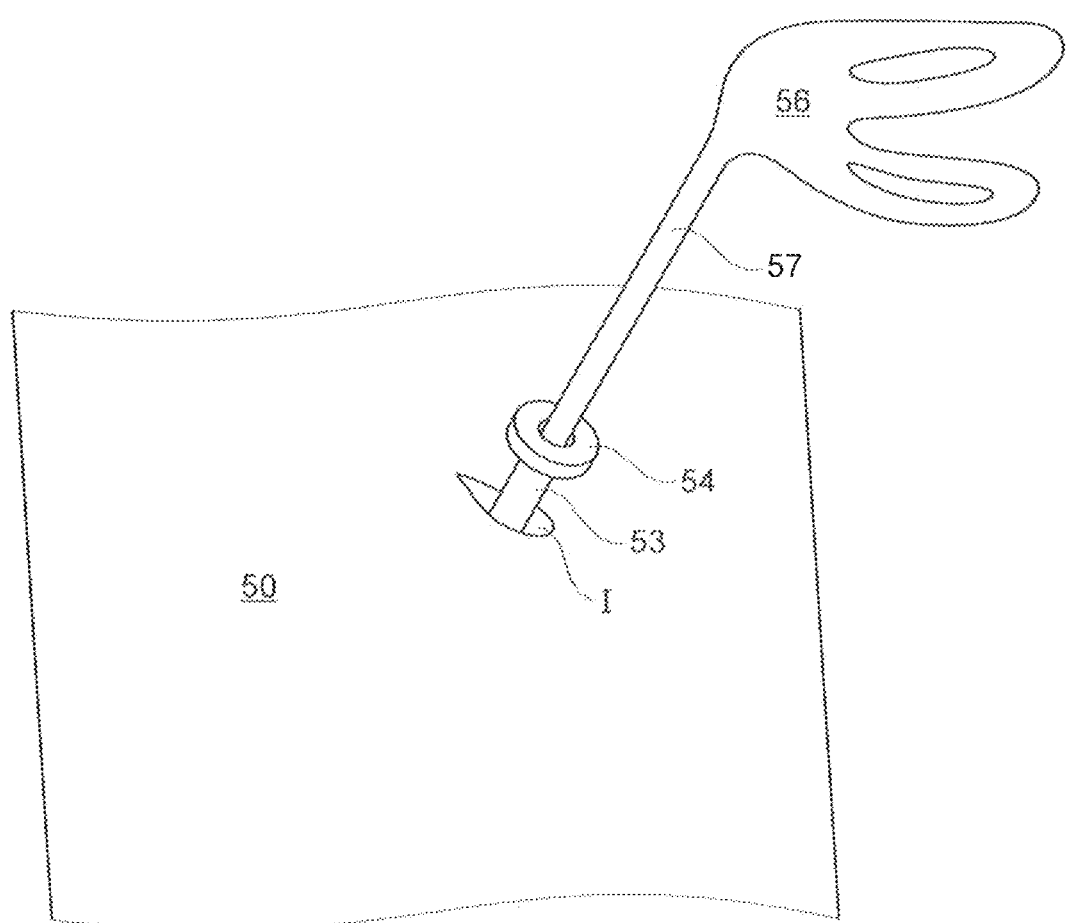
FIG. 6 is a schematic view of an embodiment of a cannula assembly kit during use in a surgical procedure seen from outside the body cavity.
Figure 7:
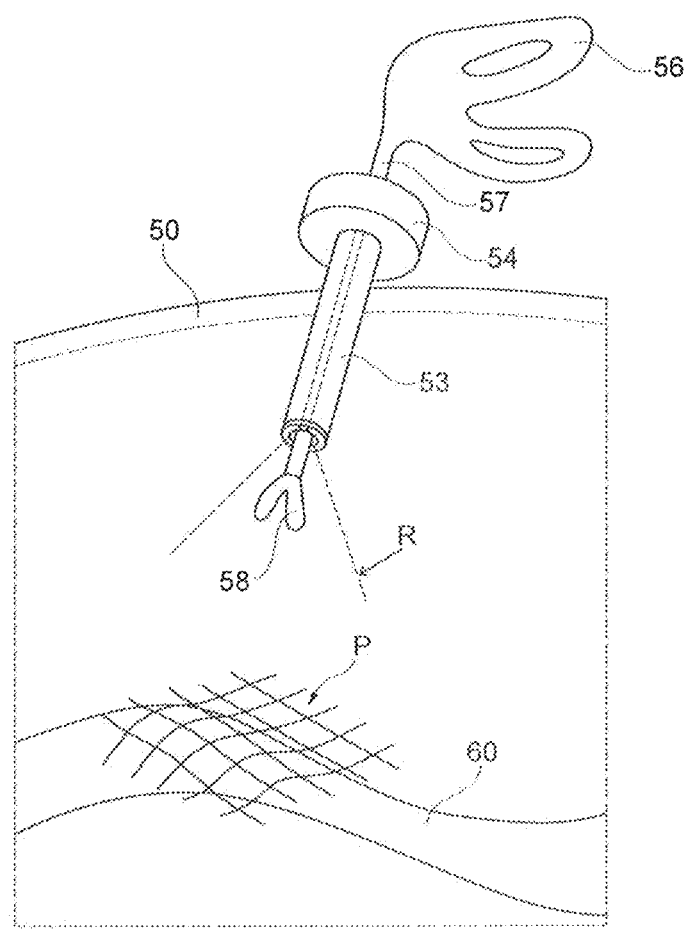
FIG. 7 is a schematic view of an embodiment of a cannula assembly kit during use in a surgical procedure seen in a cross-sectional view through the body cavity.

FIG. 6 and FIG. 7 show a cannula assembly kit in use during a surgical procedure. The figures show a body part of a patient in surgery, where an incision I is made through the skin 50 of the patient, the cannula assembly kit comprises a shaft portion 53 and a flange portion 54, and the shaft portion 53 is inserted through the incision I. The cannula assembly kit comprises a pattern generating member comprising a projector from where a light pattern P in the form of rays R of light is emitted.

A surgical instrument comprising a handle portion 56, a body portion 57 and a surgical tool 58 is inserted through the access port of the cannula assembly kit and the pattern P is projected onto a surgical site 60.

It can be seen that when the surgical tool 58 of surgical instrument is subjected to a lateral movement and/or tilting movement the pattern will be moved in a correlated way, thereby providing information to the operator.

The pattern can for example be recorded by an image recorder on a scope inserted via the same or another incision through the skin.

Figure 8:
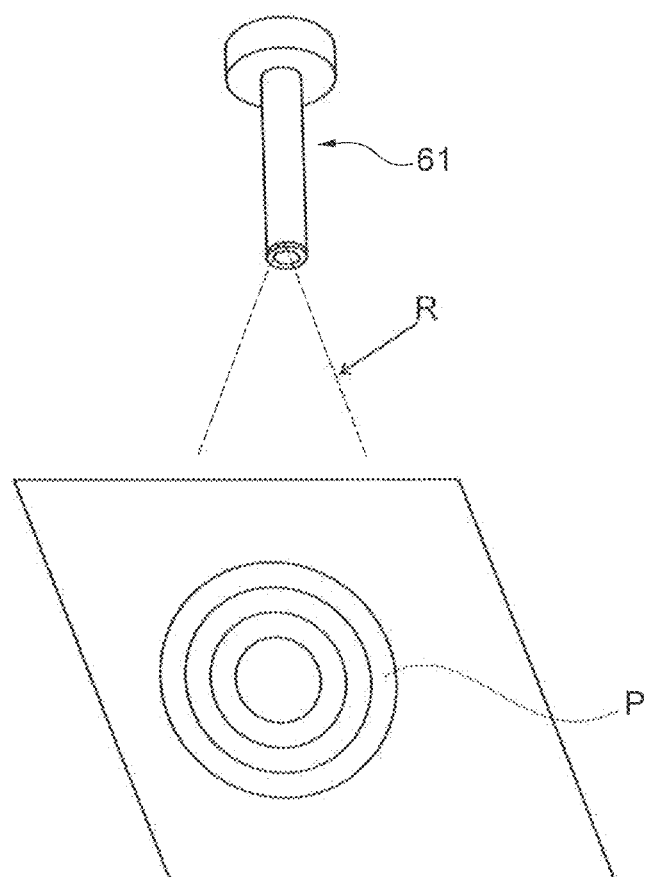
FIG. 8 is a schematic view of an embodiment of a cannula assembly kit configured for emitting a bullseye shaped pattern.

The cannula assembly kit 61 shown in FIG. 8 comprises a not shown projector operatively connected to a light source and configured for emitting light rays R arranged to form a bullseye shaped pattern P. The various rings of the bullseye shaped pattern P could for example have different wavelength profile.

Figure 9:
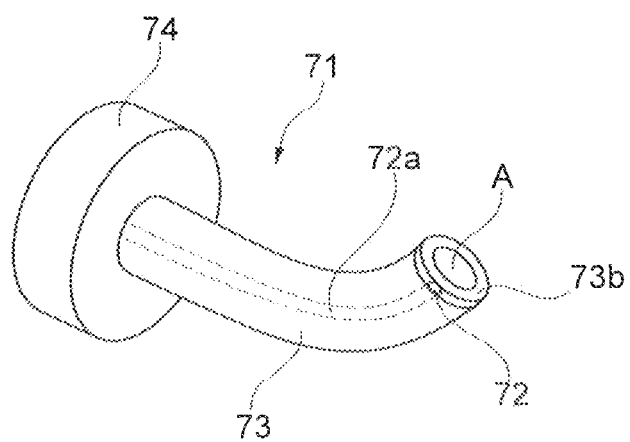
FIG. 9 is a schematic view of an embodiment of a cannula assembly kit with a bent cannula shaft portion.

The cannula assembly kit shown in FIG. 9 comprises a cannula and a pattern generating member wherein only the projector 72 is shown. The cannula comprises a flange portion 74 and an elongate cannula shaft portion 73 extending from the flange portion 74 to its distal end and an access port A. The cannula shaft portion 73 is bent in a soft curve to thereby make is easier for an operator to insert the cannula shaft portion 73 through an incision of a patient. The cannula shaft portion 73 is for example pre-bent to the shown bending curve and is further bendable or flexible i.e. in unloaded condition the cannula shaft portion 73 is bent. In another embodiment the cannula shaft portion 73 is substantially rigid in the bent position.

At its distal end the cannula shaft portion 73 comprises an end edge 73b and the projector 72 is mounted at the end edge 73b and a not shown optical fiber is arranged to guide light along a channel 72a in the wall of the cannula shaft portion 73.

Figure 10:
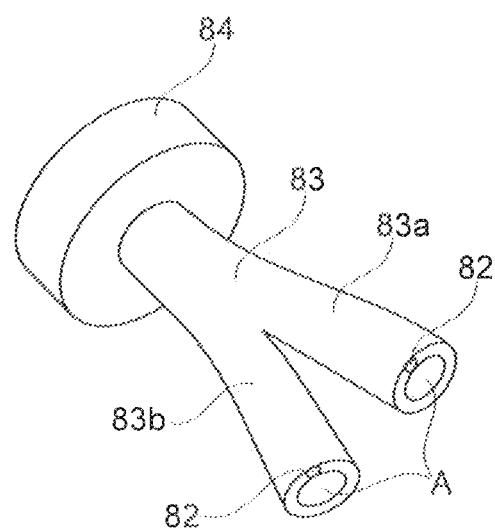
FIG. 10 is a schematic view of an embodiment of a cannula assembly kit where the cannula comprises two cannula shaft portions and one cannula flange portion.

The cannula assembly kit shown in FIG. 10 comprises a cannula and at least one pattern generating member wherein only the two projectors 82 are shown. The two projectors 82 can be of a common pattern generating member or they can be of separate pattern generating members.

The cannula comprises a flange portion 84 and a double cannula shaft portion 83, 83a, 83b. The double cannula shaft portion 83, 83a, 83b comprises a common shaft portion section 83 and two branch shaft portion sections 83a and 83b each comprising a distal access port section A, such that the cannula has a common access port section through the flange portion 84 and through the common shaft portion section 83 and two separate distal access port sections through said respective branch shaft portion sections 83a and 83b.

Figure 11:
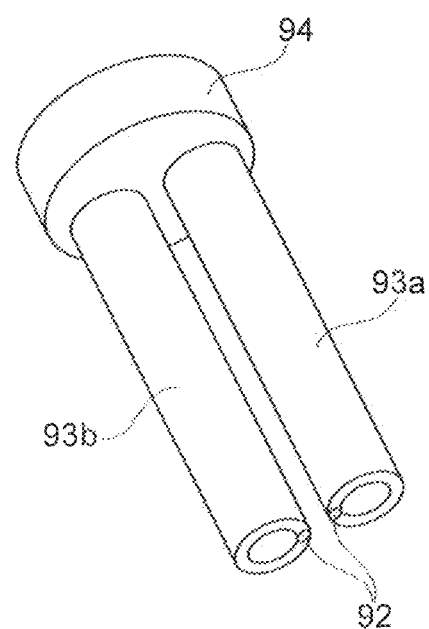
FIG. 11 is a schematic view of another cannula assembly kit where the cannula comprises two cannula shaft portions and one cannula flange portion.

The cannula assembly kit shown in FIG. 11 comprises a cannula and at least one pattern generating member wherein only the two projectors 92 are shown. The two projectors 92 can be of a common pattern generating member or they can be of separate pattern generating members.

The cannula comprises a flange portion 94 and two cannula shaft portions 93a, 93b providing two access ports through the cannula flange portion 94.

Figure 12:
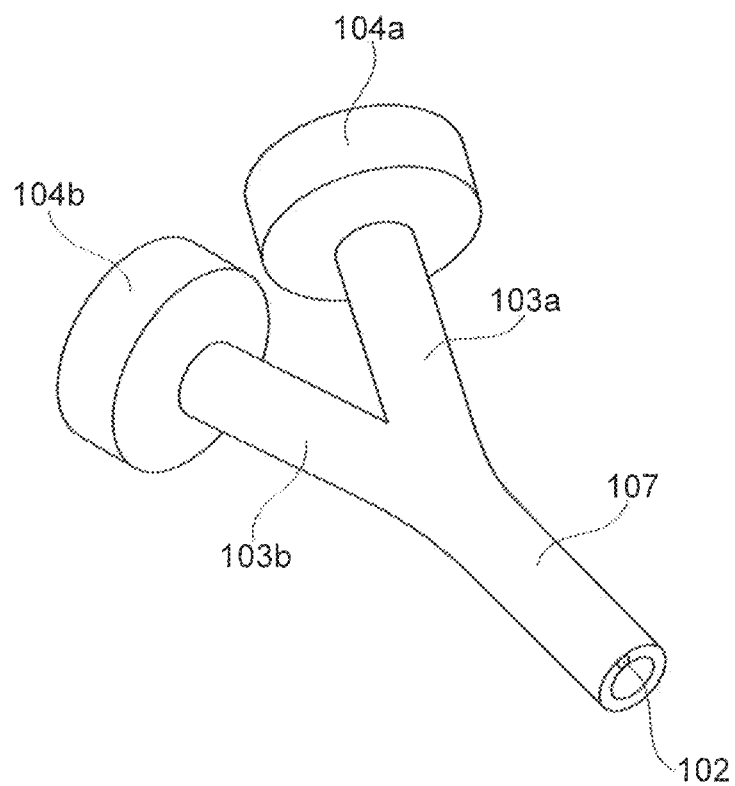
FIG. 12 is a schematic view of an embodiment of a cannula assembly kit where the cannula comprises two cannula flange portions and one cannula shaft portion.
Figure 13:
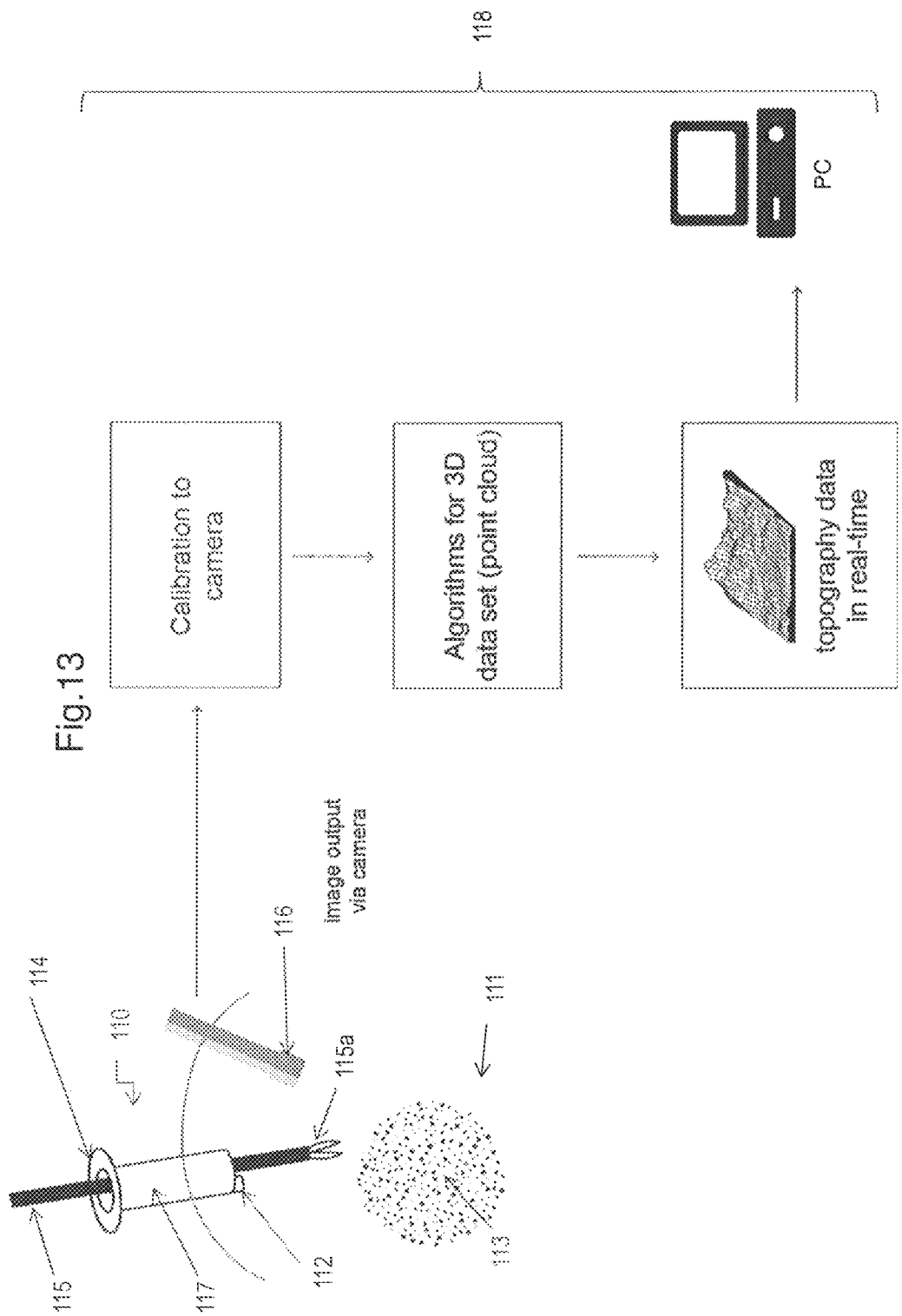
FIG. 13 is a schematic illustration of an embodiment of a minimally invasive surgery system of the invention where the projected light pattern comprises a coded structured light configuration comprising a plurality of light dots with different sizes.

The cannula assembly kit shown in FIG. 12 comprises a cannula and at least one pattern generating member wherein only the projector 102 is shown.

The cannula comprises two flange portions 104a, 104b and a double cannula shaft portion 104, 104a, 104b. The double cannula shaft portion 104, 104a, 104b comprises a common shaft portion section 104 and two branch shaft portion sections 104a and 104b. The respective branch shaft portion sections 104a and 104b are connected to the respective flange portions 104a, 104b and are merged in the common shaft portion section 104 in the distal end section of the cannula.

The minimally invasive surgery system shown in the respective FIGS. 13, 14, 15 and 16 comprises a cannula assembly kit 110, a surgical instrument 115, a camera 116 and a computer system 118.

The cannula assembly kit 110 comprises a flange portion 114, an elongate cannula shaft portion 117 and a projector 112 for projecting a light pattern at its distal end. An access port is provided via the cannula shaft portion 117.

The surgical instrument 115 comprises its actual operation tool 115a at its distal end. The distal end comprising the operation tool 115a is inserted through the access port of the cannula assembly kit 110.

The projector 112 projects a light pattern towards a distally arranged surface 111 and the reflected light pattern 113 is recorded by the camera 116. In use this distally arranged surface 111 will be a surgery site which may be very uneven as described above.

As the surgical instrument 115 is moved the cannula assembly kit will be moved accordingly and thereby also the projector 112 will be moved and the reflected pattern 113 will change accordingly at least when the surgical instrument 115 is subjected to tilting movements.

The camera records the reflected light and generates recorded image data. The recorded image data is transmitted to the computer system 118.

In the shown embodiment the computer system comprises a calibration unit for calibration of the camera, a processing unit comprising algorithms for 3D data set generation and decoding of the recorded and calibrated image data, a processing unit for determine topography data in real time and a PC for storing and/or displaying the determined topography data. The various units of the computer system 118 may be integrated in a common hardware box.

As described above the surgical instrument 115 may advantageously form part of a robot for performing the minimally invasive surgery and the computer system may provide feedback to the robot and/or at least a part of the computer system may be an integrated part of the robot.

In FIG. 17 the projected light pattern comprises a coded structured light configuration comprising a plurality of light dots with different sizes.

Figure 14:
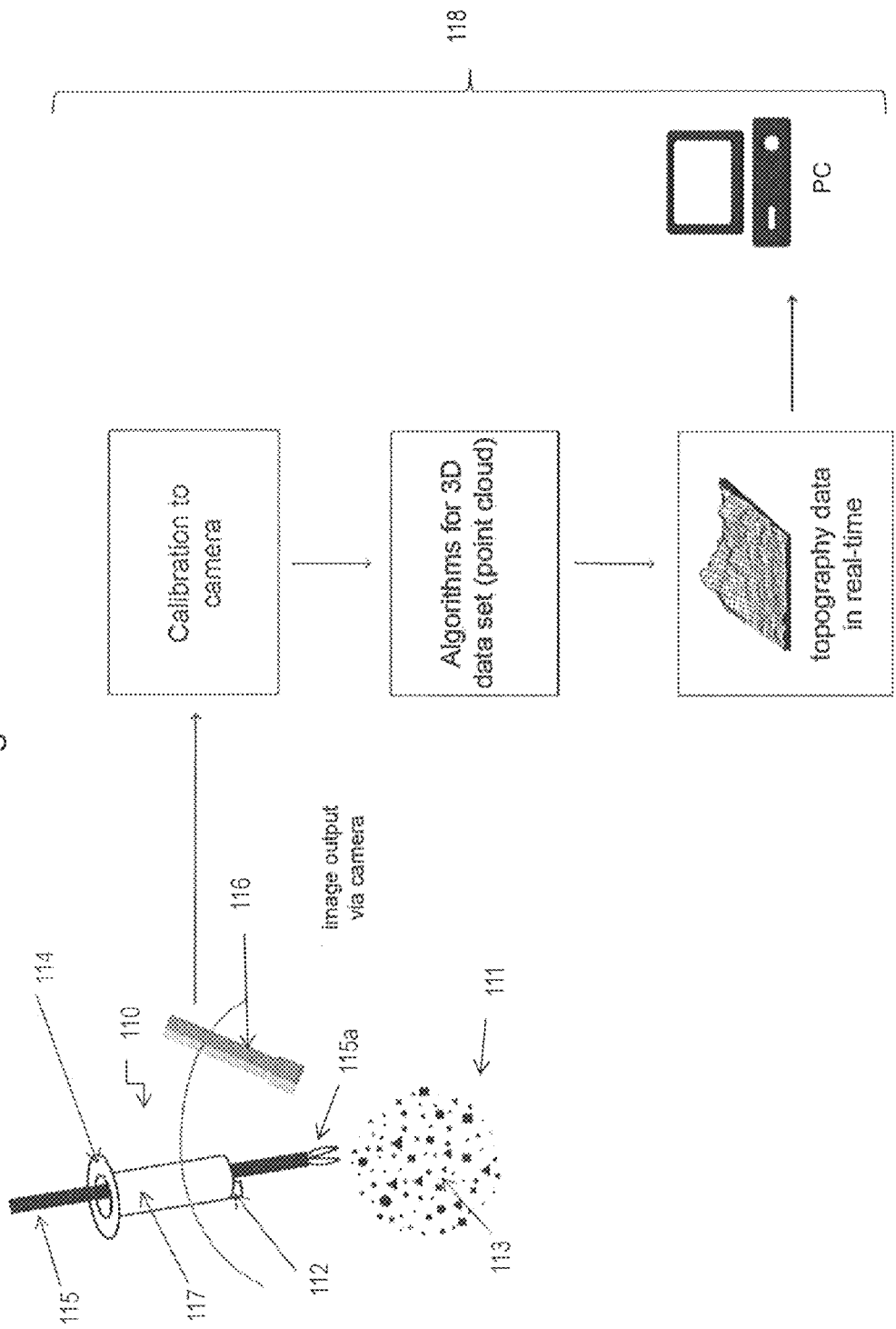
FIG. 14 is a schematic illustration of an embodiment of a minimally invasive surgery system of the invention where the projected light pattern comprises a coded structured light configuration comprising a plurality of light dots with different shapes and sizes.

In FIG. 14 the projected light pattern comprises a coded structured light configuration comprising a plurality of light dots with different shapes and sizes.

Figure 15:
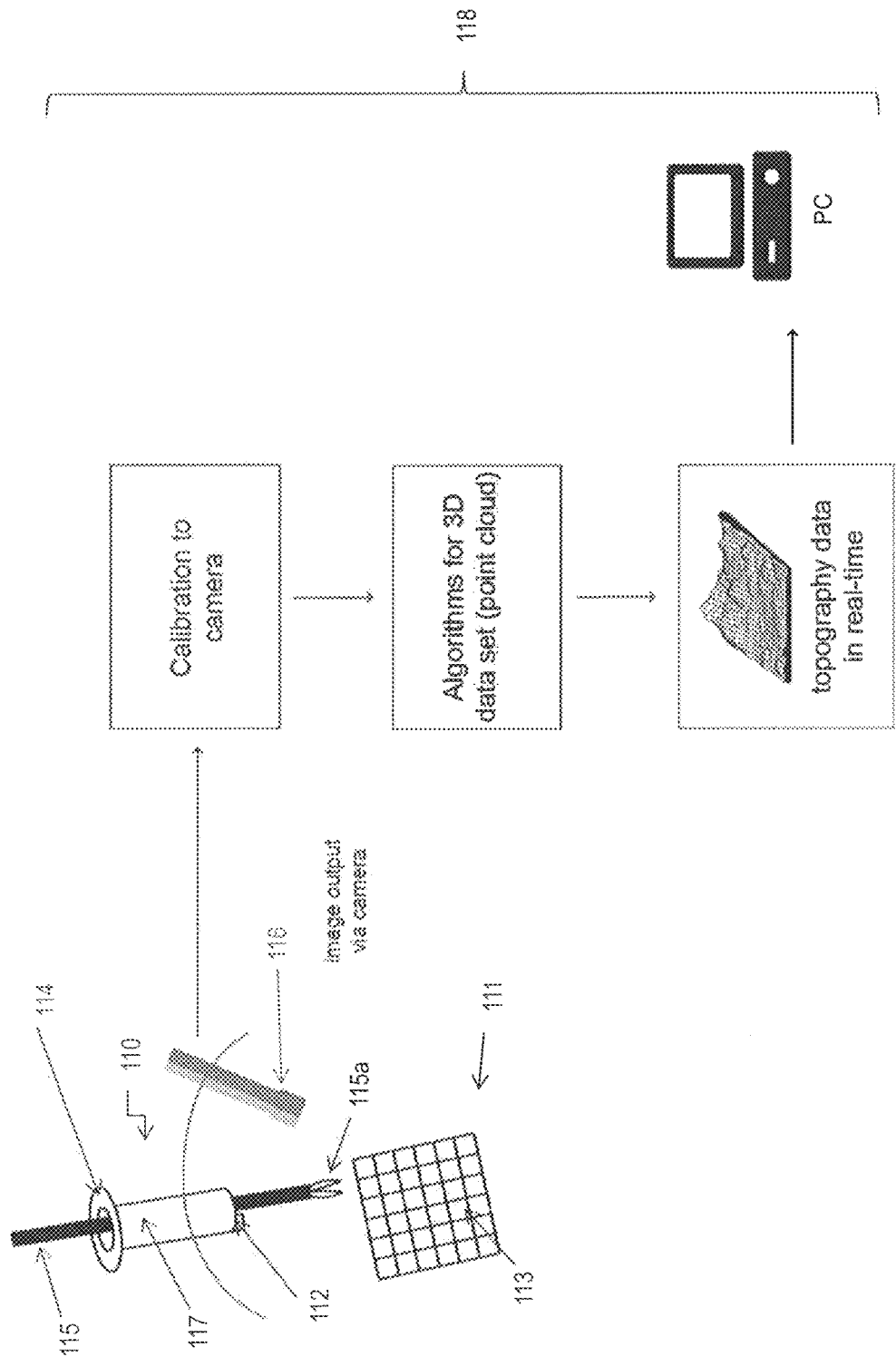
FIG. 15 is a schematic illustration of an embodiment of a minimally invasive surgery system of the invention where the projected light pattern comprises a crosshatched pattern

In FIG. 15 the projected light pattern comprises cross-hatched pattern

Figure 16:
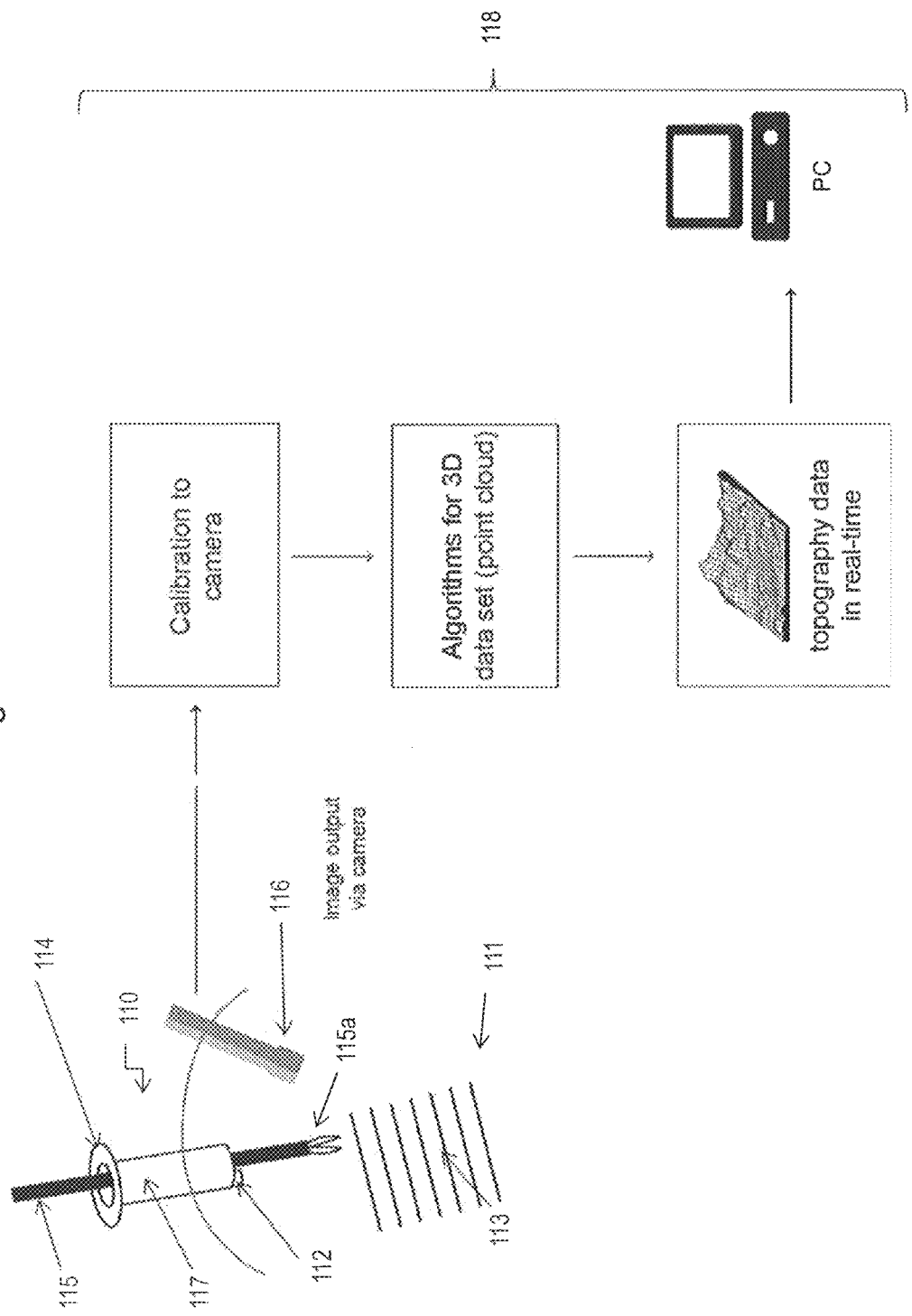
FIG. 16 is a schematic illustration of an embodiment of a minimally invasive surgery system of the invention where the projected light pattern comprises a plurality of parallel lines.

In FIG. 16 the projected light pattern comprises a plurality of parallel lines.

What is claimed is:

1. A cannula assembly kit comprising:
    a cannula having a distal end and a proximal end and an elongate cannula shaft portion extending from the proximal end to the distal end, the elongate cannula shaft portion having a sidewall and an access port extending through the elongate cannula shaft portion; and
    a projector disposed within the sidewall of the cannula shaft portion of the cannula and including a computer-regulated optical element configured to project a light pattern from the distal end of the cannula, the light pattern received from a pattern light source in operable communication with the projector and configured to create the light pattern,
    wherein the cannula includes a flange portion at the proximal end, and wherein the pattern light source is fixed to the flange portion.

2. The cannula assembly kit of claim 1, wherein the distal end of the cannula shaft portion has a distal access port exit and comprises an end edge adjacent the distal access port exit, the projector configured for being fixed at the end edge and arranged for projecting said light pattern in a distal direction.

3. The cannula assembly kit of claim 1, wherein the cannula shaft portion comprises an access section adapted to be inserted through a surgical incision for allowing a surgical instrument to be inserted through the access port, wherein at least the access section is rigid.

4. The cannula assembly kit of claim 1, wherein the cannula comprises a mounting through hole for mounting the projector to provide that the projector can be mounted at the distal end of the cannula shaft portion.

5. The cannula assembly kit of claim 1, wherein said projector comprises a phase optic element, a spatial light modulator, a multi-order diffractive lens, a holographic lens, a Fresnel lens, and/or a mirror arrangement.

6. The cannula assembly kit of claim 1, wherein the projector is configured for emitting at least one of a pattern comprising a plurality of light dots, an arch shape, ring or semi-ring shaped lines, a plurality of angled lines and a coded structured light configuration.

7. The cannula assembly kit of claim 1, wherein the projector is configured for emitting a pattern comprising a combination of lines and dots in a coded structured light configuration.

8. A trocar assembly kit comprising a cannula assembly kit and an obturator, the cannula assembly kit comprising a cannula having a distal end and a proximal end with a flange portion and an elongate cannula shaft portion extending from the proximal end to the distal end and an access port through said elongate cannula shaft portion, and a projector configured for being fixed to the cannula shaft portion of the cannula, configured to receive a light pattern, and including a computer-regulated optical element configured to project the light pattern from the distal end of the cannula, the light pattern received from a pattern light source in operable communication with the projector and configured to create the light pattern, the obturator having a distal end and a proximal end and comprising a head portion at its proximal end, a tip portion at its distal end and a rigid obturator shaft portion extending between the head portion and the tip portion, wherein the cannula and the obturator are correlated to each other to provide that the tip portion can be inserted through the access port and the head portion can be temporarily fixed to the flange portion,
    wherein the pattern light source is fixed to the flange portion.

9. The trocar assembly kit of claim 8, wherein the obturator comprises a projector protection arrangement correlated with the projector of the cannula assembly kit to at least partly cover the projector when the cannula assembly kit and the obturator are in an assembled state.

10. The trocar assembly kit of claim 9, wherein the projector protection arrangement is arranged to be pivotally folded from a first position where it is at least partly covering the projector to a second position where it at least partly is passed into a cavity of the obturator.

11. The trocar assembly kit of claim 9, wherein the projector protection arrangement is arranged to be radially displaced from a first position where it is at least partly covers the projector to a second position where it at least partly is passed into a cavity of the obturator.

12. The cannula assembly kit of claim 1, wherein the projector is a singular projector.

13. The trocar assembly kit of claim 8, wherein the projector is singular.

14. The cannula assembly kit of claim 1, further comprising the pattern light source, the pattern light source configured to create the light pattern.

15. The trocar assembly kit of claim 8, further comprising the pattern light source, the pattern light source configured to create the light pattern.

16. The cannula assembly kit of claim 14, wherein the pattern light source is at least one of a coherent light source and an incoherent light source.

* * * * *